(12) United States Patent
Ding et al.

(10) Patent No.: US 11,287,424 B2
(45) Date of Patent: Mar. 29, 2022

(54) CALIBRATING ASSAYS USING REACTION TIME

(71) Applicant: ORTHO-CLINICAL DIAGNOSTICS, INC., Raritan, NJ (US)

(72) Inventors: Zhong Ding, Pittsford, NY (US); Edward R. Scalice, Penfield, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 286 days.

(21) Appl. No.: 15/886,974

(22) Filed: Feb. 2, 2018

(65) Prior Publication Data

US 2018/0156791 A1 Jun. 7, 2018

Related U.S. Application Data

(62) Division of application No. 14/081,158, filed on Nov. 15, 2013, now Pat. No. 9,885,712.

(Continued)

(51) Int. Cl.
*G01N 33/558* (2006.01)
*G01N 33/557* (2006.01)
(Continued)

(52) U.S. Cl.
CPC ...... *G01N 33/558* (2013.01); *B01L 3/502746* (2013.01); *G01N 33/5302* (2013.01);
(Continued)

(58) Field of Classification Search
CPC ............ G01N 33/558; G01N 21/8483; G01N 21/8494; G01N 33/543; G01N 33/54306;
(Continued)

(56) References Cited

U.S. PATENT DOCUMENTS 4,539,295 A * 9/1985 Blough, Jr. .............. C12Q 1/00
422/82.05
5,120,643 A 6/1992 Ching et al.
(Continued)

FOREIGN PATENT DOCUMENTS

CN 101144811 A 3/2008
CN 101790687 A 7/2010
(Continued)

OTHER PUBLICATIONS

Chinese Office Action for CN 201380070527.5; dated: Nov. 9, 2017; 13 pages.
(Continued)

*Primary Examiner* — Melanie Brown
(74) *Attorney, Agent, or Firm* — K&L Gates LLP; Louis C. Cullman; Dennis A. Majewski

(57) ABSTRACT

A method for performing an assay on a liquid sample for the detection of one or more analytes of interest in an assay device having a flow path which includes a sample zone and detection zone thereon includes: dispensing the sample onto the sample zone; combining the sample and a reagent, wherein the sample and reagent may be combined prior to addition of the sample to the sample zone or on the assay device, flowing the combined sample/reagent by capillary action into and through the detection zone having capture elements bound thereto, wherein a signal at least partially representative of the presence or concentration of analyte(s) is produced and detected; determining a reaction time or reaction volume; and determining the concentration of the analyte by using both the detected signal and the reaction time or reaction volume.

16 Claims, 13 Drawing Sheets

Related U.S. Application Data

(60) Provisional application No. 61/726,626, filed on Nov. 15, 2012.

(51) Int. Cl.
  *G01N 33/53*  (2006.01)
  *G01N 33/543*  (2006.01)
  *B01L 3/00*  (2006.01)

(52) U.S. Cl.
  CPC ..... *G01N 33/543* (2013.01); *G01N 33/54306* (2013.01); *G01N 33/557* (2013.01); *B01L 2300/0825* (2013.01); *Y10T 436/10* (2015.01)

(58) Field of Classification Search
  CPC ..... G01N 2035/00108; B01L 3/502746; B01L 2300/0825; Y10T 436/10
  See application file for complete search history.

(56) References Cited

U.S. PATENT DOCUMENTS

| | | |
|---|---|---|
| 5,210,778 A | 5/1993 | Massart |
| 5,552,997 A | 9/1996 | Massart |
| 5,559,041 A | 9/1996 | Kang et al. |
| 5,569,608 A | 10/1996 | Sommer |
| 5,714,389 A | 2/1998 | Charlton et al. |
| 6,139,800 A | 10/2000 | Chandler |
| 6,228,660 B1 | 5/2001 | May et al. |
| 6,258,548 B1 | 7/2001 | Buck |
| 6,372,542 B1 | 4/2002 | Martin et al. |
| 6,436,721 B1 | 8/2002 | Kuo et al. |
| 6,448,067 B1 | 9/2002 | Tajnaföi |
| 6,519,542 B1 | 2/2003 | Giannuzzi et al. |
| 6,541,266 B2 | 4/2003 | Modzelewski et al. |
| 6,733,682 B1 | 5/2004 | Bjorkman et al. |
| 6,811,736 B1 | 11/2004 | Ohman et al. |
| 6,884,370 B2 | 4/2005 | Ohman et al. |
| 6,885,883 B2 | 4/2005 | Parris et al. |
| 7,118,916 B2 | 10/2006 | Matzinger |
| 7,175,992 B2 | 2/2007 | Fong |
| 7,192,784 B2 | 3/2007 | Nadaoka et al. |
| 7,416,700 B2 | 8/2008 | Buechler et al. |
| 7,604,593 B2 | 10/2009 | Parris et al. |
| 7,618,369 B2 | 11/2009 | Hayter et al. |
| 7,678,566 B2 | 3/2010 | Miyoshi et al. |
| 7,691,595 B2 | 4/2010 | Fong |
| 7,888,125 B2 | 2/2011 | Gibbons et al. |
| 8,116,740 B2 | 2/2012 | van der Haar et al. |
| 8,224,415 B2 | 7/2012 | Budiman |
| 8,252,593 B2 | 8/2012 | Fukuma et al. |
| 8,501,155 B2 | 8/2013 | Hess et al. |
| 8,507,295 B2 | 8/2013 | Caterer |
| 2002/0026110 A1 | 2/2002 | Parris et al. |
| 2002/0146835 A1 | 10/2002 | Modzelewski et al. |
| 2003/0119203 A1 | 6/2003 | Wei et al. |
| 2004/0136871 A1 | 7/2004 | Paehl ............ G01N 21/8483 422/82.05 |
| 2005/0130249 A1 | 6/2005 | Parris et al. |
| 2006/0285996 A1 | 12/2006 | Ohman et al. |
| 2006/0289787 A1 | 12/2006 | Ohman et al. |
| 2007/0048807 A1 | 3/2007 | Song |
| 2007/0065952 A1 | 3/2007 | Harris et al. |
| 2007/0148717 A1 | 6/2007 | Fong |
| 2007/0231883 A1 | 10/2007 | Lindstrom et al. |
| 2008/0081977 A1 | 4/2008 | Hayter et al. |
| 2009/0093968 A1 | 4/2009 | Kawamata et al. |
| 2009/0142781 A1* | 6/2009 | Shimizu ............ G01N 21/76 435/7.92 |
| 2009/0208975 A1* | 8/2009 | D'Costa ............ B01L 3/5023 435/7.2 |
| 2010/0023291 A1 | 1/2010 | Hayter et al. |
| 2010/0049022 A1 | 2/2010 | Parris et al. |
| 2010/0061894 A1 | 3/2010 | Yamauchi |
| 2010/0105142 A1 | 4/2010 | Fukuma et al. |
| 2010/0191085 A1 | 7/2010 | Budiman |
| 2010/0267065 A1 | 10/2010 | Geiger et al. |
| 2011/0053289 A1 | 3/2011 | Lowe et al. |
| 2011/0124127 A1 | 5/2011 | Caterer |
| 2012/0071342 A1 | 3/2012 | Lochhead ......... G01N 21/6452 506/9 |
| 2012/0283960 A1 | 11/2012 | Budiman |

FOREIGN PATENT DOCUMENTS

| | | |
|---|---|---|
| JP | 2001-318100 | 11/2001 |
| JP | 2003-004743 | 1/2003 |
| JP | 2007-040939 | 2/2007 |
| JP | 2008-170190 | 7/2008 |
| JP | 2009-47590 | 3/2009 |
| JP | 2010-008107 | 1/2010 |
| JP | 2010-117290 | 5/2010 |
| WO | WO 99/18426 | 4/1999 |
| WO | WO 01/88534 A2 | 11/2001 |
| WO | WO 02/070734 A1 | 9/2002 |
| WO | WO 03/103835 A1 | 12/2003 |
| WO | WO 2005/089082 A2 | 9/2005 |
| WO | WO 2005/118139 A1 | 12/2005 |
| WO | WO 2006/137785 A1 | 12/2006 |
| WO | WO 2007/007849 A1 | 1/2007 |
| WO | WO 2007/087439 A2 | 8/2007 |
| WO | WO 2007/149042 A1 | 12/2007 |
| WO | WO 2008/042760 A2 | 4/2008 |
| WO | WO 2009/019230 A2 | 2/2009 |
| WO | WO 2010/088569 A1 | 8/2010 |

OTHER PUBLICATIONS

Japanese Office Action for JP 2015-542829; dated Sep. 12, 2017; 9 pages.
Russian Office Action and Search Report for RU 2015121732; dated Oct. 2, 2017; 15 pages.
Chinese Office Action and Search Report for CN 201380070527.5; dated Feb. 20, 2017; 15 pages.
U.S. Appl. No. 61/588,738, filed Jan. 20, 2012; Title: Assay Device Having Multiple Reagent Cells; 39 pages.
U.S. Appl. No. 61/588,758, filed Jan. 20, 2012; Title: Low Volume Assay Device Having Increased Sensitivity; 38 pages.
U.S. Appl. No. 61/588,779, filed Jan. 20, 2012; Title: Assay Device Having Multiplexing; 45 pages.
U.S. Appl. No. 61/588,745, filed Jan. 20, 2012; Title: Assay Device Having Uniform Flow Around Corners; 37 pages.
U.S. Appl. No. 61/588,772, filed Jan. 20, 2012; Title: Controlling Fluid Flowthrough an Assay Device; 45 pages.
U.S. Appl. No. 61/588,899, filed Jan. 20, 2012; Title: Assay Device Having Controllable Sample Size; 32 pages.
Supplementary European Search Report for EP Application No. 13 854 265.9; dated Sep. 20, 2016; 14 pages.
A mathematical model of lateral flow bioreactions applied to sandwich assays; Shizhi Qian and Haim H. Bau; Analytical Chemistry; vol. 322, No. 1; Nov. 1, 2003; pp. 89-98; 10 pages.
Office Action issued in related Chinese Patent Application No. 201380070527.5 daated May 16, 2018 and English translation of same.

* cited by examiner

CALIBRATING ASSAYS USING REACTION TIME

CROSS REFERENCE TO RELATED APPLICATIONS

This patent application is a divisional application of U.S. patent application Ser. No. 14/081,158, filed Nov. 15, 2013, which claims priority upon U.S. Patent Provisional Application Ser. No. 61/726,626, filed Nov. 15, 2012, the entire contents of each application being incorporated herein by reference.

FIELD OF THE INVENTION

The present invention relates to the field of diagnostic assays, and in particular to lateral flow assays where an analyte to be detected is present in a biological or non-biological sample.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture. Understandably it is difficult to meet all these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a reagent zone also known as a conjugate zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising, e.g., cellulose, wool, glass fiber, asbestos, synthetic fibers, polymers, or mixtures of the same.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

A known non-porous assay device is shown in FIG. 1. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay. Unbound dissolved conjugate material will be swept past the detection zone into the at least one wicking zone 5. Also shown in FIG. 1 are projections or micropillars 7. An instrument such as that disclosed in US 20060289787A1, US20070231883A1, U.S. Pat. Nos. 7,416,700 and 6,139,800 all incorporated by reference in their entireties, are able to detect the bound conjugated material in the detection zone. Common labels include fluorescent dyes that can be detected by instruments which excite the fluorescent dyes and incorporate a detector capable of detecting the fluorescent dyes.

In order to produce a reportable result from a measured signal, e.g., a fluorescent signal, a calibration curve needs to be formulated to correlate the measured signal to the concentration of the analyte of interest in the sample being analyzed. Developing a calibration curve is well known in the art and does not need detailed explanation. Briefly, multiple samples having known varying concentrations of analyte (also called calibrator fluids) are run on an assay device in a manner similar to an end user performing an assay on a sample having an unknown concentration of analyte. The signal produced by the analyte signal producing complex, such as an analyte/labeled antibody conjugate, is read and recorded as a data point for each of the multiple samples. The data points are plotted on a curve of concentration versus signal strength. The data points can then be curve fit into an equation that provides analyte concentration as a function of signal strength for that particular assay. For example, a linear correlation can be represented by $C=mS+b$, where C is the concentration of the analyte, S is the measured signal and m and b are experimentally determined constants. Non-linear correlations can be represented with non-linear mathematical models such as the log it/log 4 relationship.

For many commercially available assays, the calibration curve is developed at the factory where the assay is made. Due to variation in raw materials and other factors when an assay is made, a different lot-specific calibration curve may be developed for each lot of assays produced. The calibration curve data can then be included in each lot of assay sold to an end user. Alternatively, a calibration curve is automatically created by the customer's analyzer when the customer runs a calibration process with the lot of assay material, their analyzer, and a series of calibrator materials provided by the manufacturer.

When making a calibration curve at a factory, a standard calibrator fluid is used to approximate the characteristics of the actual samples that will be used by the end user of the assay device. For example, if the assay will be used with plasma samples, the calibrator fluid will generally be formulated to mimic the characteristics of a typical plasma sample. This should result in the unknown concentration of the analyte in the sample being assayed being the same as the concentration of the analyte in the calibrator fluid for equivalent measured signals.

A typical measured signal for lateral flow assays is a peak height or peak area of a trace of fluorescent intensity vs. distance along the detection zone. However, it is sometimes the case where the measured signal in sample does not depend on concentration alone. Other factors, particularly for capillary driven lateral flow assays devices, in addition to analyte concentration, can affect the measured signal. If these factors are not taken into account, then the measured signal for a sample being assayed will not accurately correlate to the true concentration of analyte in the sample. This of course, can have profound effects, e.g., on a patient's diagnosis or prognosis.

Accordingly, there is a need for a method that can take into account other factors that affect the measured signal of a capillary driven lateral flow assay device.

SUMMARY OF THE INVENTION

The present invention is directed to an assay device that alleviates one or more the foregoing problems described above.

One aspect of the invention is directed to a method for performing an assay on a liquid sample for the detection of one or more analytes of interest in an assay device having a flow path which includes a sample zone and detection zone thereon. The method includes: dispensing the sample onto the sample zone; combining the sample and a reagent, wherein the sample and reagent may be combined prior to addition of the sample to the sample zone or on the assay device, flowing the combined sample/reagent by capillary action into and through the detection zone having capture elements bound thereto, wherein a signal at least partially representative of the presence or concentration of analyte(s) is produced and detected; determining a reaction time; and determining the concentration of the analyte by using both the detected signal and the reaction time.

Another aspect of the invention is directed to a method of calibrating an assay. The method includes: (a) providing multiple calibrator fluids having known concentrations of analyte therein, (b) providing an assay device having a substrate that include a sample zone and detection zone, wherein the method further includes: (c) dispensing one of the calibrator fluids onto the sample zone; (d) combining the calibrator fluid and a reagent, wherein the calibrator fluid and reagent may be combined prior to addition of the calibrator fluid to the sample zone or on the assay device; (e) flowing the combined calibrator fluid/reagent by capillary action into and through the detection zone having capture elements bound thereto, wherein a signal at least partially representative of the presence or concentration of analyte(s) is produced and detected; (f) determining a reaction time; (g) repeating steps (b)-(f) for each calibrator fluid; and (h) using the detected signal S, the reaction time t and the known concentrations C to determine a calibration curve.

According to another aspect of the invention, there has been provided a method for performing an assay on a liquid sample for the detection of one or more analytes of interest in an assay device having a flow path which includes a sample zone and detection zone thereon. The method includes: dispensing the sample onto the sample zone; combining the sample and a reagent, wherein the sample and reagent may be combined prior to addition of the sample to the sample zone or on the assay device, flowing the combined sample/reagent by capillary action into and through the detection zone having capture elements bound thereto, wherein a signal at least partially representative of the presence or concentration of analyte(s) is produced and detected; determining a reaction volume; and determining the concentration of the analyte by using both the detected signal and the reaction volume.

According to still another aspect of the invention, there has been provided a method of calibrating an assay. The method includes: (a) providing multiple calibrator fluids having known concentrations of analyte therein; (b) providing an assay device having a substrate that include a sample zone and detection zone: (c) dispensing one of the calibrator fluids onto the sample zone; (d) combining the calibrator fluid and a reagent, wherein the calibrator fluid and reagent may be combined prior to addition of the calibrator fluid to the sample zone or on the assay device, (e) flowing the combined calibrator fluid/reagent by capillary action into and through the detection zone having capture elements bound thereto, wherein a signal at least partially representative of the presence or concentration of analyte(s) is produced and detected; (f) determining a reaction volume; (g) repeating steps (b)-(f) for each calibrator fluid; (h) using the detected signal S, the reaction volume and the known concentrations C to determine a calibration curve.

Further objects, features and advantages of the present invention will be apparent to those skilled in the art from detailed consideration of the preferred embodiments that follow.

DETAILED DESCRIPTION OF PREFERRED EMBODIMENTS

Figure 1:
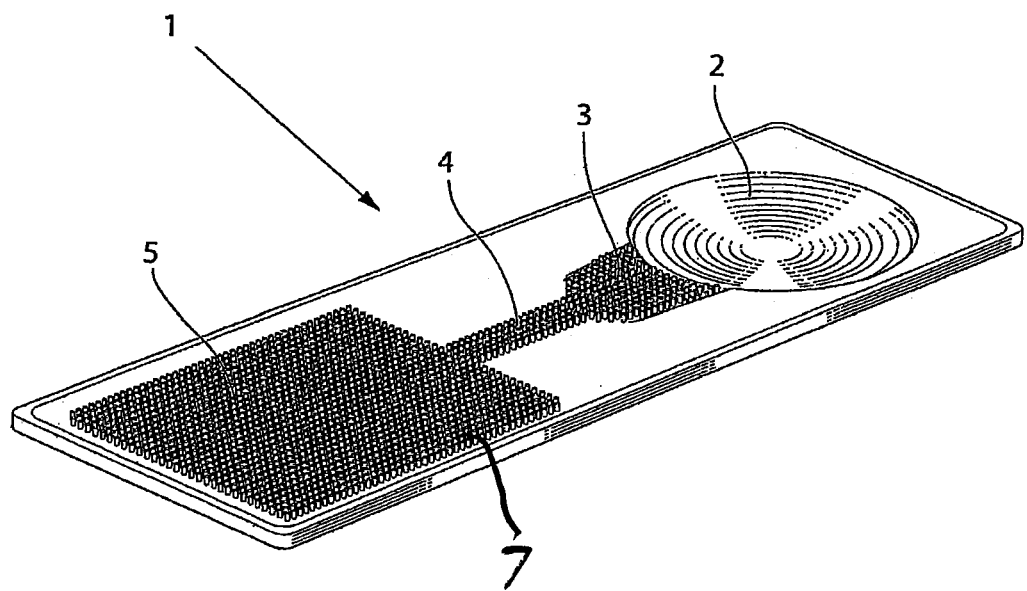
FIG. 1 shows a schematic view of a known assay device usable with the present invention.

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

The determination based on lateral flow of a sample and the interaction of components present in the sample with reagents present in the device or added to the device during the procedure and detection of such interaction, either qualitatively or quantitatively, may be for any purpose, such as diagnostic purposes. Such tests are often referred to as lateral flow assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device usable with the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The terms "zone", "area" and "site" are used in the context of this description, examples and claims to define parts of the fluid flow path on a substrate, either in prior art devices or in a device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

Figure 2:
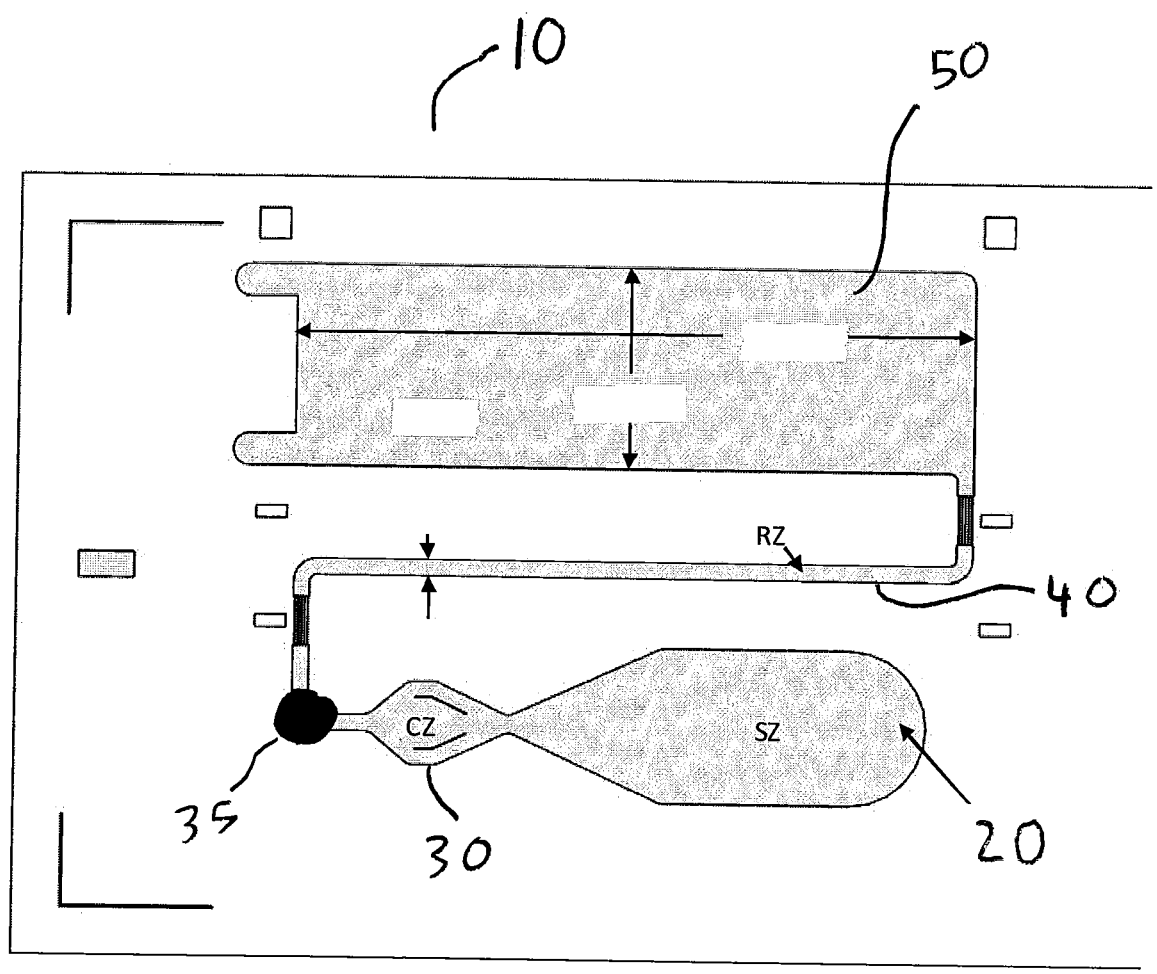
FIG. 2 shows a schematic view of an assay device usable with the present invention.
Figure 3:
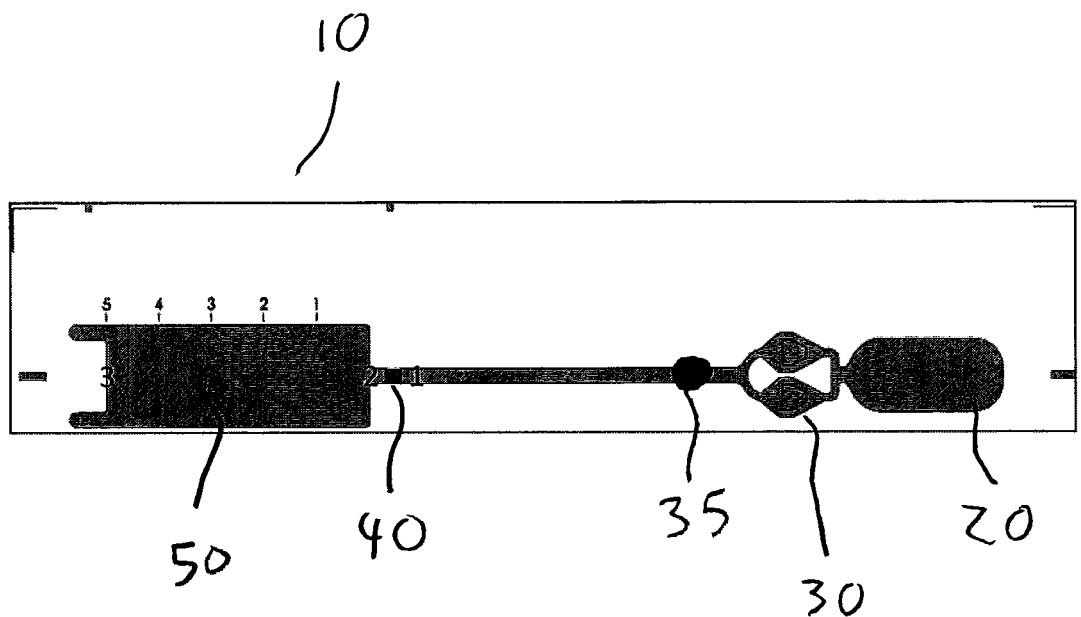
FIG. 3 shows a schematic view of an assay device usable with the present invention.

FIGS. 2 and 3 show a schematic view of a preferred embodiment of such devices according to the invention. The assay device 10, has at least one sample addition zone 20, at least one reagent zone 30, at least one detection zone 40, and at least one wicking zone 50. The zones form a flow path by which sample flows from the sample addition zone to the wicking zone. Also included are capture elements in the detection zone 40, capable of binding to the analyte, optionally deposited on the device (such as by coating); and a labeled reagent material also capable of binding to the analyte or the capture element, located on the device in the reagent zone, wherein the labeled reagent material carries a first label for detection in the detection zone.

Components of an assay device (i.e., a physical structure of the device whether or not a discrete piece from other parts of the device) usable in the present invention can be prepared from copolymers, blends, laminates, metalized foils, metalized films or metals. Alternatively, device components can be prepared from copolymers, blends, laminates, metalized foils, metalized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

In one embodiment, the flow path is non-porous and can include open or closed paths, grooves, and capillaries. In one preferred embodiment, the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 1 shows projections 7.

In one embodiment the flow path is at least partially open. In another embodiment the flow path is entirely open. Open means that there is no lid or cover at a capillary distance. Thus the lid, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably 30 to about 100 µm, and a gap or gaps between the projections of about 3 to about 200 µm, preferably 5 to 50 µm from each other. The flow channel may have a length of about 2 to about 100 mm, preferably about 5 to about 50 mm, and a width of about 0.1 to about 5 mm, preferably about 0.5 to 1.2 mm.

In another embodiment, the flow path is porous and includes a porous material, e.g., nitrocellulose, defining the flow path capable of supporting capillary flow. Examples include those shown in U.S. Pat. Nos. 5,559,041, 5,714,389, 5,120,643, and 6,228,660 all of which are incorporated herein by reference in their entireties.

The liquid sample zone 20, also referred to as the liquid sample addition zone, receives sample from a sample dispenser, such as a pipette. The sample is typically deposited onto the top of the zone. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, described above, or preferably through projections, such as micro-pillars, as shown in FIG. 1 and also described above. In those devices that can use finger stick volumes of blood, the sample can be directly touched off from the finger, or by a capillary pipette.

A filter material (not shown) can be placed in the sample addition zone to filter particulates from the sample or to filter blood cells from blood so that plasma can travel further through the device.

Located between the sample addition zone and the detection zone is a reagent zone 30. The reagent zone can include reagent(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. The amount of reagent in the reagent zone can be adjusted by the length of reagent deposited into the device while maintaining the same reagent width. The amount of reagent can also be adjusted by changing the width while maintaining the length. The amount of reagent can further be adjusted by changing both width and length simultaneously. In one preferred embodiment, the reagent zone includes conjugate material. The term conjugate means any moiety bearing both a detection element and a binding partner. Alternatively, the reagents, including the detection element and conjugate, can be added to the sample prior to addition to the sample addition zone. If all reagents are combined with the sample prior to the sample addition zone, then of course, a separate reagent zone will not be necessary.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}I$ and $^{32}P$.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in an "sandwich" assay, the binding partner in the conjugate can form a complex including the analyte and the detection element and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 35 in FIGS. 2 and 3. The reagent addition zone can allow addition of a reagent externally from the device. For example, the reagent addition zone may be used to add an interrupting reagent that may be used to wash the sample and other unbound components present in the fluid flow path into the wicking zone. In a preferred embodiment the reagent addition zone 35 is located after the reagent zone 30. According to a preferred embodiment, the reagent plume from the reagent zone should be as wide as possible to cover as much of the width of the detection zone as possible. One preferred embodiment for increasing the width of the reagent plume is described in co-pending application entitled "Assay Device Having Multiple Reagent Cells" (Ser. No. 61/588,738, first named inventor: Zhong Ding) filed Jan. 20, 2012, which is incorporated herein by reference in its entirety. In summary, multiple areas having reagent material (hereinafter referred to as "reagent cells") in a reagent zone along with elements to recombine multiple flow streams that result from the multiple reagent cells into one flow stream results in a more desirably mixed, wider reagent plume as it leaves the reagent zone and enters the detection zone.

Downstream from the liquid sample zone and the reagent zone is the detection zone 40 which is in fluid communication with the sample addition zone. The detection zone 40 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in co pending application entitled "Lower Volume Assay Device Having Increased Sensitivity" (Application No. 61/588,758, first named inventor: Phil Hosimer) filed Jan. 20, 2012 and incorporated by reference in its entirety, are significantly narrower, e.g., 1.5 mm or less.

The detection zone is where any detectable signal is read. In a preferred embodiment attached to the projections in the detection zone are capture elements. The capture elements can include binding partners for the reagent or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. As noted above, the conjugate can be pre-deposited on the assay device, such as by coating in the reagent zone. Similarly the capture elements can be pre-deposited on the assay device on the detection zone. Preferably, both the detection and capture elements are pre-deposited on the assay device, on the detection zone and reagent zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the reagent zone or those added through the reagent addition zone. The reagent plume can include the conjugate having both the detection element and binding partner, in which case it is often referred to as a conjugate plume.

As described above, a problem facing the inventors and others in the art was to accurately and precisely correlate the measured signal in a lateral flow assay to the actual concentration of analyte in the sample. The predicted concentration of an analyte in the sample based on a calibration curve performed prior to the actual analysis, such as at the factory sometimes deviated from the actual concentration, sometimes by significant amounts. Something other than concentration of analyte was affecting the signal being measured by the instrument. As described above, in a lateral flow assay the analyte containing sample is combined with a detection element upstream from a detection zone, where it then flows into the detection zone and the detection element or a complex containing the detection element is captured and the signal produced by the detection element is measured by the instrument.

Figure 4:
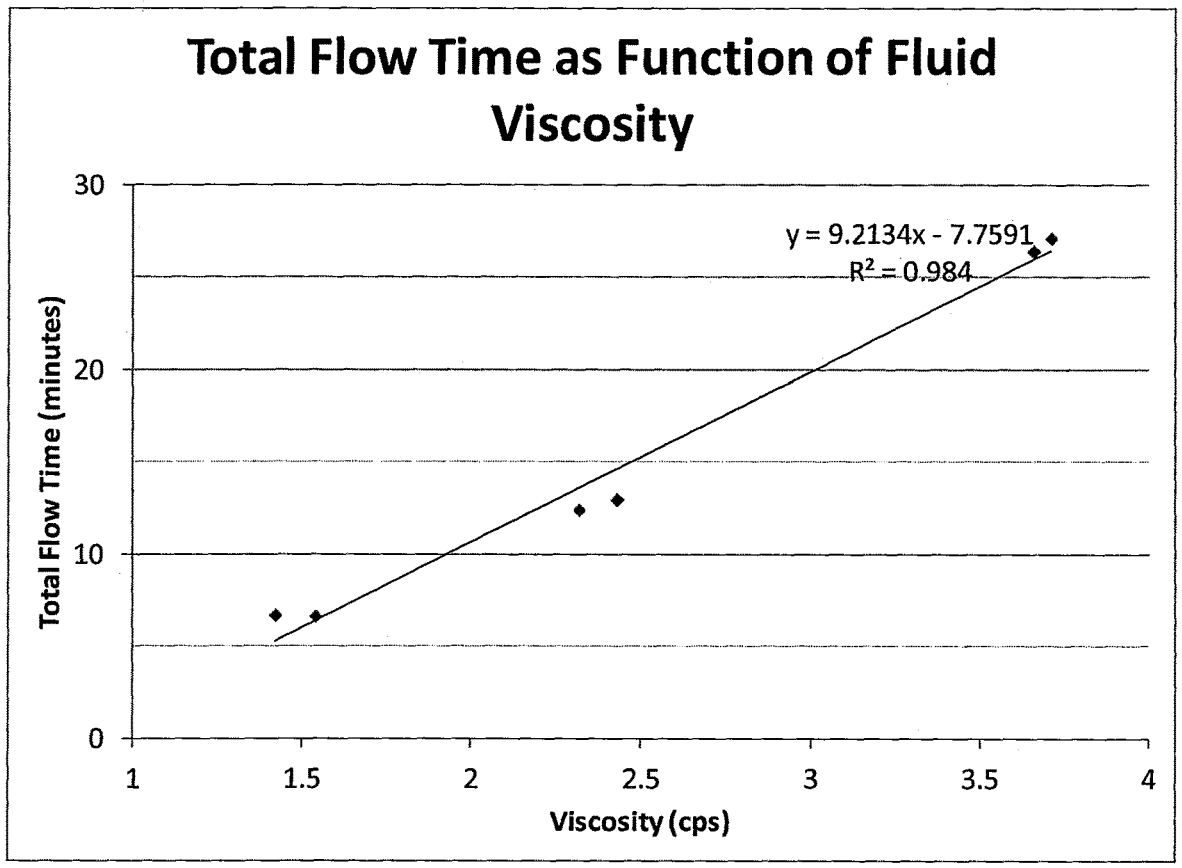
FIG. 4 is a graph showing the relationship between total flow time in an assay device and viscosity.

Samples that differ in viscosity will have differing flow rates or flow times in lateral flow devices relying on capillary forces to drive fluid flow. FIG. 4 shows the linear relationship between viscosity and total flow time for the lateral flow device shown in FIGS. 2 and 3. The present inventors have found that in lateral flow assay device, signal generated by two samples of equal concentration but having differing flow times will be different, assuming all other conditions are the same, e.g., same device design, amount of detection element deposited, etc. This is believed to be due to the time the detection element (generally conjugated with a binding partner as described above) is allowed to interact with analyte in the sample (for sandwich assays), and the time the detection element or a complex containing the detection element is allowed to interact with and bind with the capture element in the detection zone.

As explained above, in a lateral flow assay device the sample containing the detection element in the reagent plume flows into the detection zone. As the sample flows through the detection zone, the detection element, which is a function of analyte concentration, is brought into contact with the capture elements mainly through diffusion. This diffusion occurs as the detection element in the flow stream passes by those features (e.g., microposts or fibers) of the lateral flow device having the capture element bound thereto. After sample containing the detection element (e.g., the conjugate plume) passes through the detection zone, remaining sample or an added wash passes through the detection zone and washes unbound detection element out of the detection zone. The bound detection element is then read by the instrument and the signal is recorded. The ability of the detection element to diffuse from the flow stream to the bound capture element will depend on many factors, chief among them, is the amount of time the conjugated detection element is in proximity to the bound capture element. As noted above, the amount of time the detection element (directly or otherwise) has to interact with the analyte can also affect signal, all though to a much lesser degree than the interaction with the capture element. Thus, a longer flow time will put the detection element in proximity to the capture element for a longer time and thus, provide more opportunity for the conjugated detection element to diffuse to the bound capture element. The amount of detection element that binds to the capture element will then depend on the concentration of analyte, and the ability of the detection element to diffuse from the flow stream to the fixed capture element. The signal measured or detected by the instrument depends on the amount of conjugated detection element in the detection zone.

If the fluid characteristics (e.g., viscosity) between the calibrator fluid used to calibrate the assay and the sample fluid being assayed are different, a different amount of signal will result even for the same concentration of analyte. This being due to the differing ability of (i.e., amount of time) the conjugated detection element to diffuse from the flow stream to the fixed capture element as described above. Accordingly, the present inventors determined that a calibration curve needed to be able to take into account fluid flow time through the assay device and its effect on signal strength, and not only on analyte concentration. Thus, instead of detected signal S being a function of concentration C only (S=$f$(C)), the detected signal is a function of both concentration and flow time t (S=g(C,t)). Accordingly, a broad aspect of the invention provides a method for determining the concentration of an analyte in a sample that accounts for both concentration and flow time.

The flow time can be represented by the term "reaction time" which is broadly defined as the time that a detection element has to bind with the capture element in the detection zone. In preferred embodiments, the reaction time itself can be measured using signal generated by the detection element at points in the flow path and detected by the same instrument used to detect signal used to generate a reportable result. However, other methods for determining reaction time that do not rely on detecting signal provided by the detection element can also be used.

There are several determinable methods for measuring a representation of reaction time. One is the "reagent dissolution time," which is the time the combined sample/reagent is first detected at a point along the substrate flow path after the reagent zone to the time when the combined sample/reagent is no longer detected at that point in the substrate.

Another time proportional to or representative of the reaction time can be obtained by measuring the total flow time, which is the time it takes the sample to flow from the sample zone to the end of the wicking zone.

Another time proportional to or representative of the reaction time can also be obtained by measuring the total wick time, which is the time between sample entering the wicking zone to reaching the end of the wicking zone. This can be done by detecting signal from detection element that is washed out of the detection zone.

Alternatively, a time proportional to the reaction time can determined as the wetting time, which is the time required for a sample to completely penetrate throughout the lateral flow device.

Finally, a rate inversely proportional to the reaction time can also be determined by simply measuring the flow rate of the sample moving through the assay device. The flow rate can be measured by any known method, such as measuring the time required for the flow front to pass from one point on the device to another point on the device of known distance from the first point. For any of the above techniques to measure a representation of the reaction time, the detection element that is measured to generate a reportable result, flowing through the assay device can also be used in the measurement of the reaction time. This has the advantages of the ability to use the same instrument that is used to measure the signal which is representative of the analyte in the sample to measure the reaction time as well. No additional detectable agents, such as different labels are required. However, in some embodiments, it may be desirable to read another signal, such as using an infrared detector to detect when a portion of the assay device is wetted, etc.

Figure 5:
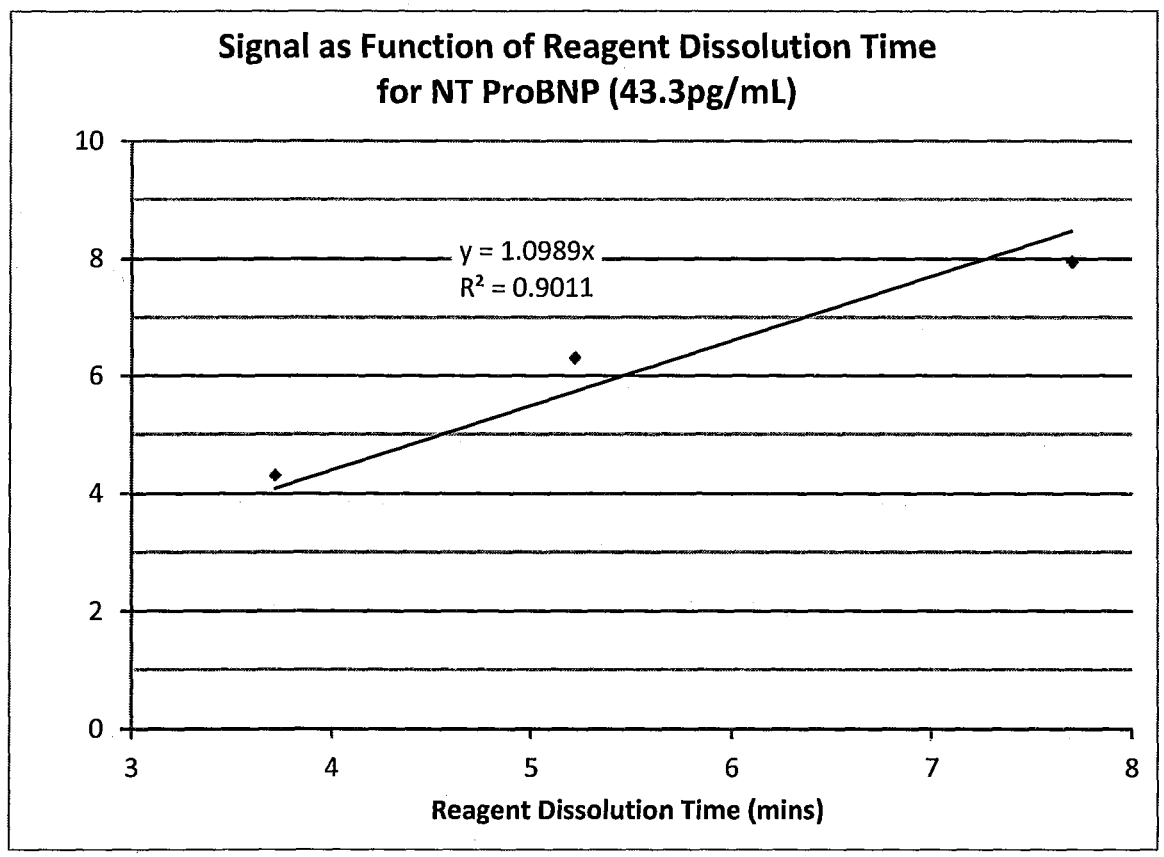
FIG. 5 is a graph showing the relationship between signal strength and reagent dissolution time for a constant concentration of NT proBNP.

FIG. 5 graphically depicts the effect that reagent dissolution time has on the amount of signal generated by samples having the same concentration of NT-proBNP (a sandwich assay) but with varying reagent dissolution rates (i.e., reaction times) caused by differing fluid viscosities. In this example, samples containing the same concentration of NT-proBNP but of differing fluid viscosities were prepared by dissolution of varying amounts of the polymer polyvinylpyrrolidone (PVP) into different aliquots of the fluid to represent patient serum samples of differing viscosity. As FIG. 5 shows, increases in reagent dissolution time results in an increased in measured signal for the same concentration of analyte.

Figure 6:
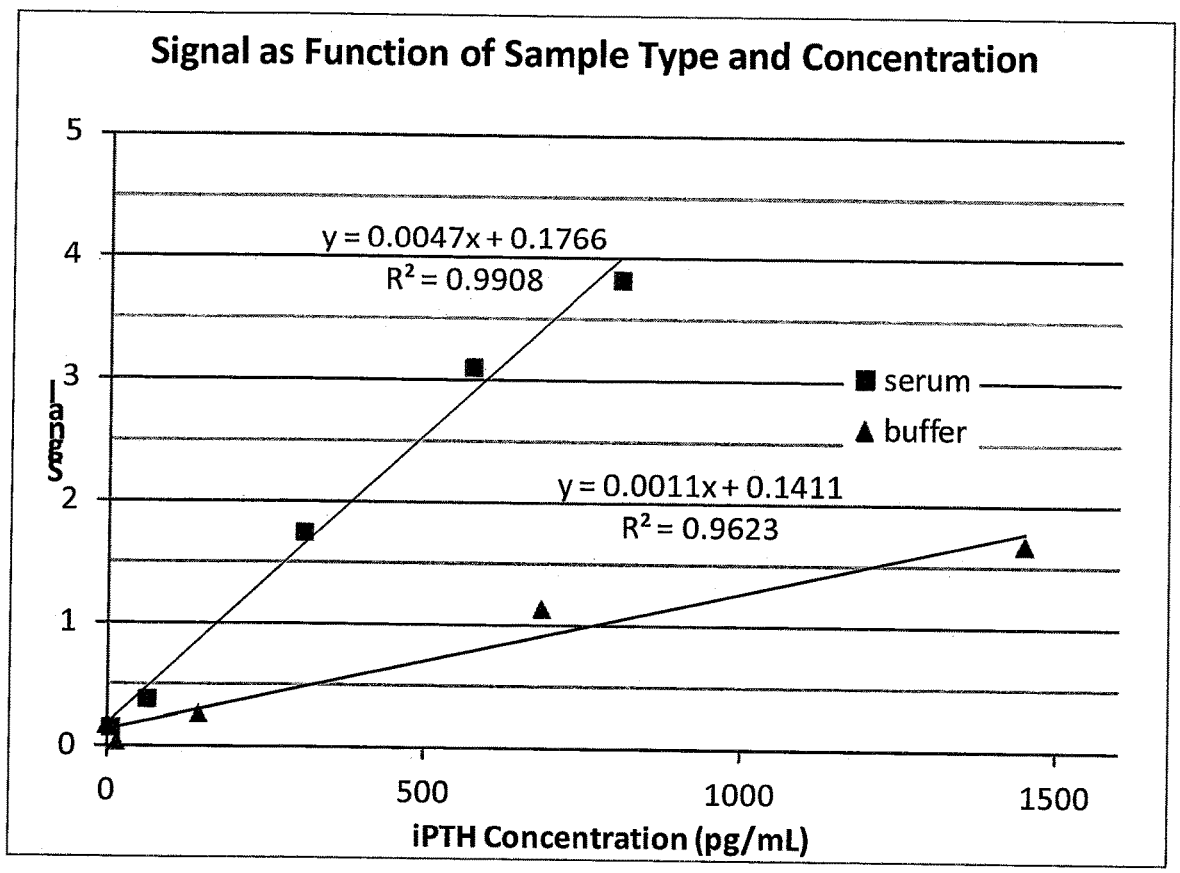
FIG. 6 is a graph which shows signal strength as a function of concentration and fluid types.

FIG. 6 shows another example of the effect of sample type on reaction time and hence on signal strength. In FIG. 6, varying concentrations of intact parathyroid hormone (iPTH), a sandwich assay, in serum (having a higher viscosity and hence longer reaction time) and buffer (lower viscosity, shorter reaction time) are plotted against signal strength. As shown in the figure, a significantly smaller signal is produced in the buffer solution as compared to the serum for the same concentration. Thus, as evident in FIGS. 5 and 6, there is a need for a method of performing an assay that takes into account both concentration and reaction time. In other words, a method is needed that minimizes the impact of reaction time variability between samples having differing fluid characteristics on the calculated concentration of the analyte.

In addition to reaction time having an effect on the detected signal, the present inventors also discovered further factors that can affect the detected signal for a given concentration of analyte. Specifically, in addition to the reaction time, reaction volume also affects the detected signal, especially for the competitive assay since a change in reaction volume leads to change in the dissolved reagent concentration (total amount of deposited reagent is the same). In a preferred embodiment, the reaction volume is determined as the product of flow rate and reaction time. When a sample is applied to an assay device, the sample will first contact the reagent in the reagent zone. As the sample flows through the reagent zone, it will dissolve reagent. Upon dissolution of the reagent, the remaining sample flowing through the reagent zone will no longer encounter reagent, and hence, will be reagent free. This portion of sample will be used to wash unbound reagent from the detection zone. Thus, there are two portions of sample. The sample used to dissolve the reagent in the reagent zone and the following portion of sample that is reagent free and is used as a wash. The portion of sample used to dissolve the reagent is called the reaction volume. As noted above, the reaction volume is preferably determined as a product of reaction time and flow rate (reaction volume=flow rate×reaction time). Thus, the discovery of reaction volume is the recognition that for some assays (e.g., competitive assay) the detected signal is dependent on reaction volume as well as analyte concentration.

Figure 7:
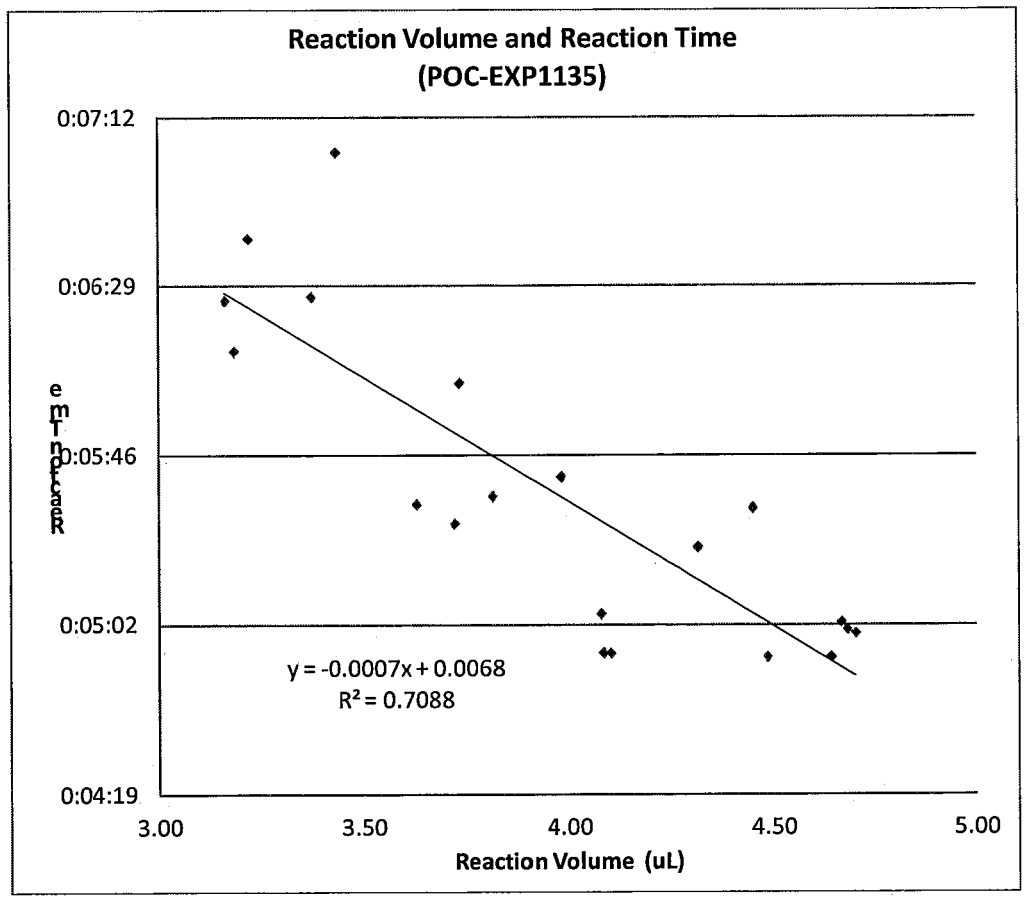
FIG. 7 is a graph showing the relationship between reaction volume and reaction time.

FIG. 7 shows the relationship between reaction volume and reaction time. As FIG. 7 demonstrates an increased reaction volume results in a decreased reaction time.

Figure 8:
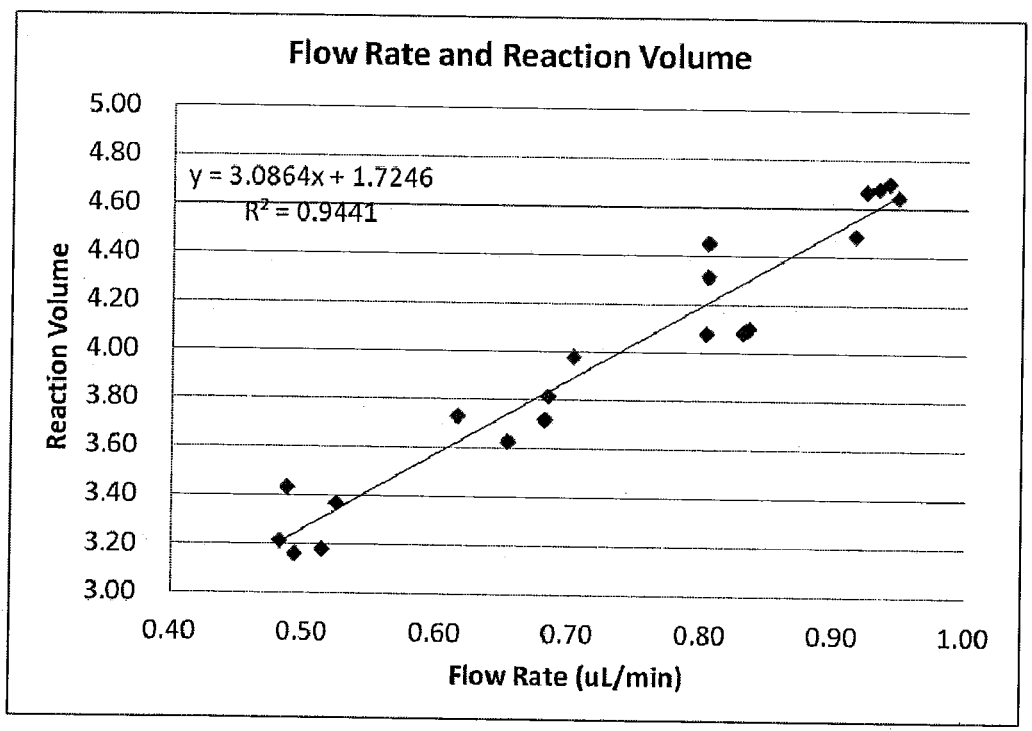
FIG. 8 is a graph showing the relationship between flow rate and reaction volume.

FIG. 8 shows the relationship between flow rate and reaction volume. As FIG. 8 demonstrates, an increased flow rate results in an increased reaction volume.

Figure 9:
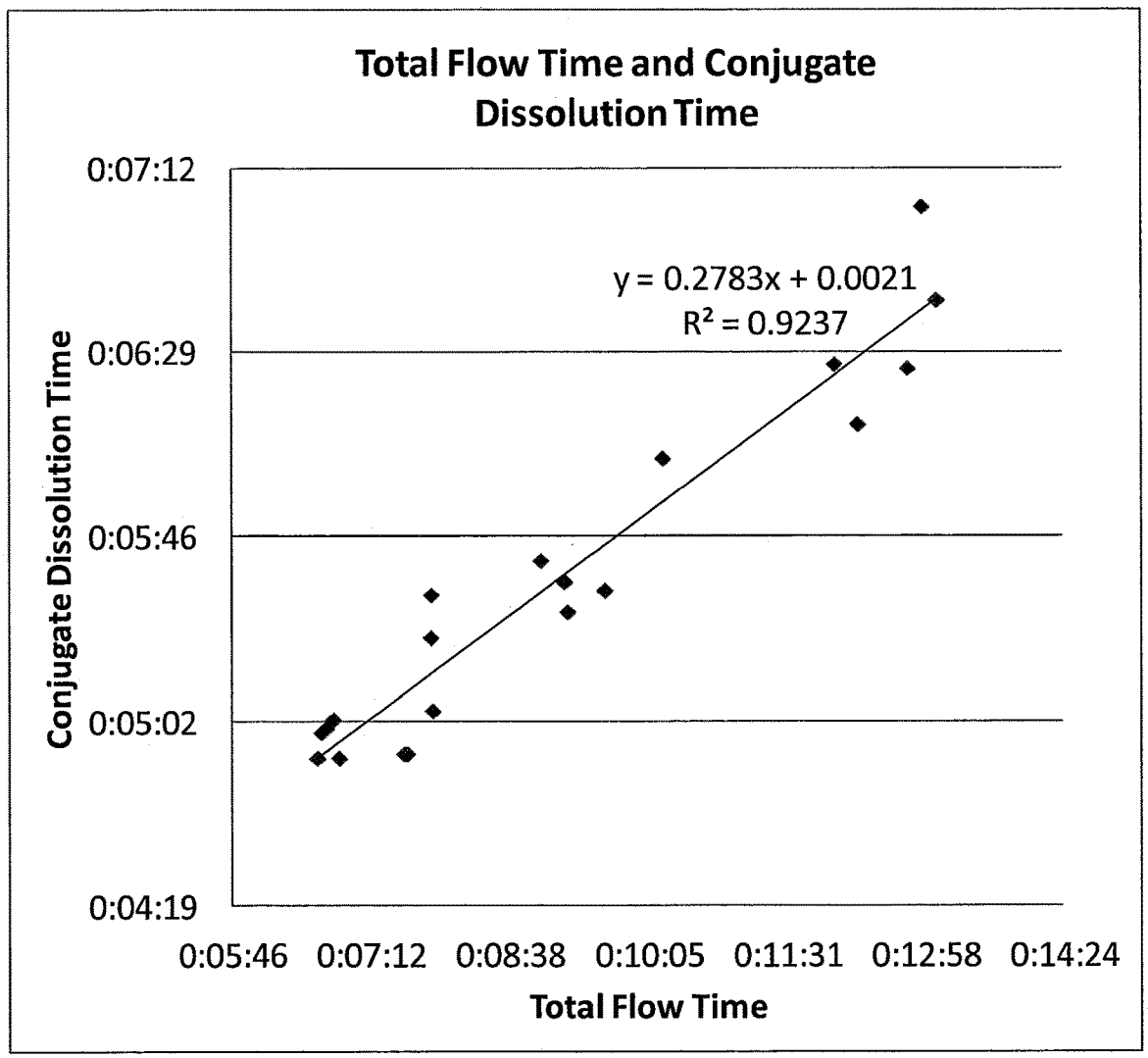
FIG. 9 is a graph showing the relationship between conjugate (i.e., reagent) dissolution time and total flow time.

FIG. 9 shows the relationship between total flow time and conjugate dissolution time (i.e., reaction time). As FIG. 9 demonstrates, an increased total flow time results in an increased conjugate dissolution time. Thus FIGS. 7-9 show a slower flow rate means longer flow time, longer reagent dissolution time and a smaller reaction volume.

As discussed above, the reaction volume is essentially the sample volume that is used to dissolve the deposited conjugate, described above, to create the sample-conjugate mixture. In a lateral flow assay, only a portion of the sample dissolves and mixes with the deposited conjugate, assuming no wash fluid is added. That portion of total sample that dissolves the conjugate (i.e., that volume of sample flowing through the reagent zone during the conjugate dissolution time) is the reaction volume.

When the flow rate is faster (i.e., viscosity is lower) the total amount of sample used to dissolve the conjugate will be larger (i.e., larger reaction volume). Therefore, the conjugate concentration will be smaller (i.e., a larger reaction volume). For a given concentration of analyte in the sample, the total amount of analyte in the reaction volume will be increased compared to a lower flow rate. The opposite applies when the flow rate is slower (i.e., viscosity is higher). That is, the total amount of sample used to dissolve the conjugate will be smaller. For a given concentration of analyte in the sample, the total amount of analyte in the reaction volume will be decreased compared to a higher flow rate.

For a sandwich type assay, the labeled conjugate in the conjugate zone is typically in significant excess (typically 100 times or more) compared to what is required to bind with the analyte. Thus, although the labeled conjugate concentration will be somewhat lower due to the larger reaction volume, this will not affect the binding of the analyte to the labeled conjugate significantly, due to the significantly larger excess of labeled conjugate. The concentration of the analyte labeled conjugate complex is therefore dominated by the analyte concentration. Therefore slightly increasing or decreasing conjugate concentration, due to flow rate variation, has only a small effect on analyte-conjugate concentration. Given the same analyte concentration, a longer reaction time lead to more binding of the analyte-conjugate complex to the pillar surface to generate signal. Therefore the signal is affected by the reaction time. Since the reaction time is also related with the reaction volume as shown in FIG. 7, the reaction volume can also be used to adjust the signal for the sandwich-type assay.

For a competitive type assay, a larger reaction volume will lead to a lower concentration of labeled analyte. Since the labeled analyte competes with the unlabeled analyte in the sample in the detection zone, the increased ratio of free analyte/labeled analyte in the sample results in less capture of the labeled analyte in the detection zone. Both concentration (and therefore the reaction volume) and reaction time affects signal. Since reaction volume and reaction time are correlated (longer reaction time corresponding to lower reaction volume), both volume adjustment method (i.e., reaction volume) and time adjustment method (i.e., reaction time) can be used.

The flow rate through a lateral flow device such as those shown in FIGS. 2 and 3 is essentially constant through the wicking zone. Thus, if the volume of the wicking zone is known and the flow time in the wicking zone is known, the flow rate can be easily calculated. For example in FIG. 3:

$t_2$ is the time for the sample fluid reaching the start of the wicking zone (location 2 in FIG. 3).
$t_3$ is the time for the sample fluid reaching the end of the wicking zone (location 3 in FIG. 3).
The volume of the wicking zone is $V_{wz}$ (μL).

The flow rate at the wicking zone is a constant and is calculated using the formula:

$$\text{flow rate} = V_{wz} \text{ (uL)}/(t_3 - t_2) \text{ (μL/min)}.$$

As noted above, once the flow rate is known the reaction volume is determined by reaction volume=flow rate×reaction time.

Using the reaction time and reaction volume, two adjustments to the signal or response of the assay can be made and are herein after called adjusted responses (or adjusted signals). As noted above, the signal itself is the peak area or the peak height obtained by scanning through the detection zone after sample flows to the end of the wicking zone.

There are two types of adjusted responses (also called adjusted signals).

Type 1, the signal or response is adjusted by multiplying the reaction volume, i.e., adjusted response=response×(reaction volume)=response×flow rate×reaction time Type 2, the signal or response is divided by the reaction time, i.e., adjusted response=response/reaction time. As the examples below show, using either adjusted responses precision can be significantly improved.

One preferred method for taking reaction time and reaction volume variability into account in determining analyte concentration is to develop a calibration curve that also accounts for variability in reaction time or reaction volume, i.e., develop an equation that recognizes that signal is both a function of concentration and reaction time or reaction volume. The calibration model (usually, but not always, carried out in the factory where the assay device is made) is determined using standard calibrator fluids having varying known concentrations and multiple assay devices. The calibrator fluids are applied to the assay devices. Signal and flow times at selected locations are measured for each calibrator fluid. The flow rate and reaction times are calculated based on the measurements. Each signal and reaction time is then used to determine a calibration model, which may be linear or a more complex non-linear as described below.

One advantage of the present invention is that fluid conditions, e.g., viscosity, are not required to be known in order to take into account the effect that fluid conditions have on reaction time. All that is required is to be able to determine some indicator of reaction time, e.g, reagent dissolution time or reaction volume.

According to one aspect of the invention, a method for performing an assay includes the steps for conducting an assay as described above, e.g., dispensing sample on the assay device, flowing the sample through the device, reading the resulting signal, etc. In addition to the above steps, the method also includes determining a reaction time and optionally a flow rate as defined above, and using both the reaction time or reaction volume and detected signal to determine the concentration of the analyte in the sample.

For the case of the type 2 adjusted response (i.e., using only reaction time), depending on the assay the function $S=f(C,t)$ can be linear or more complex non-linear functions. In one embodiment the calibration model is linear and the function can be represented by:

$$S=(\beta t+\alpha)(kC+b) \qquad (1)$$

In the above equation, S is the detected signal, t is the reaction time, α is a first constant, and β is second constant, and k is a third constant and b is the 4th constant. These constants are determined by using calibrator fluids having at least two different concentrations and at least two different reaction times using techniques that involve solving simultaneous equations that are well known in the art.

In equation (1) above, the concentration can be represented by:

$$C = \frac{1}{k}\left[\frac{S}{(\beta t + \alpha)} - b\right] \quad (2)$$

Once the constants are determined during the calibration process, the constants are included in the lot data for that particular lot of assays. In a preferred embodiment the instrument can automatically read the lot data, including the calibration constants when the assay is being performed. The instrument will also determine the reaction time in the same manner or in a manner proportional as was done during the factory calibration, e.g., as reagent dissolution time, total wick time, flow rate, etc., as well as the resulting signal when the assay is performed. Using the above equation, the instrument will report a concentration that accounts for both concentration and reaction time variability.

In a similar manner, non-linear assays can be calibrated. For example, concentration C of the analyte using the log it/log 4 math model can be represented by the equation:

$$C = e^{\left\{-\frac{1}{\beta_3}\left[\beta_2 + \ln\left(\frac{\beta_1}{\frac{S}{\beta t + \alpha} - \beta_0} - 1\right)\right]\right\}} \quad (3)$$

wherein C is concentration of the analyte, S is the signal, and $\beta_0$-$\beta_3$ are first, second, third and fourth constants, respectively. The constants $\beta_0$-$\beta_3$ are determined during the calibration procedure according to the present invention that measures both reaction time and signal strength.

In another preferred aspect of the invention, the reaction time t is accounted for in the calibration model by using the rate of signal to determine analyte concentration. The rate of signal R is defined as the signal S measured by the instrument over the reaction time t:

$$R = S/t \quad (4)$$

This is the same as the Type 2 adjusted response described above. For an assay that has a linear relationship the concentration can be expressed as:

$$C = (R - \alpha)/\beta \quad (5)$$

Where C is concentration of the analyte, R is the rate of signal, $\alpha$ is a first constant, and $\beta$ is a second constant. The constants determined during the development of the calibration model, generally done at the factory, in a similar manner as described above. The advantages of using the rate of signal method to determine analyte concentration is that fewer equations are needed during the calibration process because there are only two constants to solve for as opposed to four constants for equation (2) above.

Once the constants are determined during the calibration process, the constants are included in the lot data for that particular lot of assays. During use, the instrument can automatically read the lot data, including the calibration constants. The instrument will also determine the reaction time in the same manner as was done during the factory calibration. e.g., as reagent dissolution time, total wick time, flow rate, etc., as well as the resulting signal when the assay is performed. Using the above equation, the instrument will report a concentration that accounts for both concentration and reaction time variability.

In a similar manner, non-linear assays can be calibrated using the rate of signal R. For example, concentration C of the analyte using the log it/log 4 relationship can be represented by the equation:

$$C = e^{\left\{-\frac{1}{\beta_3}\left[\beta_2 + \ln\left(\frac{\beta_1}{R - \beta_0} - 1\right)\right]\right\}} \quad (6)$$

wherein C is concentration of the analyte, R is the rate of signal, and $\beta_0$-$\beta_3$ are first, second, third and fourth constants, respectively. The constants $\beta_0$-$\beta_3$ are determined during the calibration procedure according to the present invention that measures both reaction time and signal strength.

In a manner similar to the Type 1 adjusted response (R=S/t), the Type 2 adjusted response R=S×reaction volume, preferably R=(S*t*flow rate) can be determined using the above calibration equations.

The device usable with the present invention is preferably a disposable assay device. The assay device may be contained in a housing for ease of handling and protection. If the assay device is contained in such a housing, the housing will preferably include a port for adding sample to the assay device.

The assay device usable in the method of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another aspect of the invention is directed to a method of performing an assay on a liquid sample for the detection of one or more analytes of interest. A liquid sample containing the analyte(s) of interest is deposited onto the sample zone of the assay device, such as through a port in the housing of the device, or by touching off a finger directly onto the sample addition zone in the case of a fingerstick blood draw. The sample moves by capillary action through an optional filter, and into the reagent zone where it dissolves the reagent material. Alternatively as described above, the sample and reagent material are combined at some point prior to the detection zone. In a preferred embodiment, the sample is reacted with a detection element in the case of a sandwich-type assay, either directly or indirectly, such as through an antibody. The sample flows away from the reagent zone having a dissolved reagent plume as it flows into the detection zone.

Next the sample moves by capillary action into the detection zone. In the detection zone, a signal representative of an analyte or control is produced. In a preferred embodiment the sample or the one or more reagents having a detection element is captured in the detection zone, such as by antibodies on the surface of the detection zone and a signal representative of the presence or concentration of the analyte(s) or control(s) is produced. The reader or detection instrument as described above is then used to read the signal that is produced in the detection zone to determine the presence or concentration of the analyte(s) or control(s). The sample moves from the detection zone and into the wicking zone. The reader may read the signal in the detection zone immediately or a short time after the sample has moved through the detection zone. Also, one or more washes may follow the sample through the device to wash any unbound reagents, such as detection element, away from the detection zone. The reaction time is also determined using one of the techniques described above.

The instrument, using the lot calibration data provided with the assay, the signal read in the detection zone and the reaction time, then automatically determines the concentration of the analyte. Alternatively, the calibration model can be determined outside of a factory setting. For example, the calibration curve may be automatically created by the analyzer when the assay lot is used in conjunction with calibrators of known analyzer concentration, generally provided by the assay manufacturer. The analyzer will then use the calibration curve it created to calculate the concentration of analyte when samples are tested. Alternatively, the concentration of the analyte can be calculated manually using the equations derived above.

The method, assay device, and reader according to an embodiment of the invention have many advantages, mainly related to the improved reaction kinetics of the immunochemical reactions and the increased sensitivity of the assay.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Plastic substrate chips made of Zeonor (Zeon, Japan) having oxidized dextran on the surface for covalently immobilization of proteins via Schiff base coupling were used. Fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. Sample having the concentration of sample set out in Table 1 below was added to the sample zone of the device and the capillary action of the micropillar array distributed the sample through the flow channel into the wicking zone. To provide different reaction times, different chip designs (A and B) were used that provided the two reaction times shown in Table 1 and in FIGS. 10A and 10B. The signal intensities from the fluorescently labeled complexes in the detection zone were recorded in a prototype line-illuminating fluorescence scanner. The results are shown in FIGS. 10A and 10B described below.

TABLE 1

| Reaction | | Chip Design | | | | |
|---|---|---|---|---|---|---|
| | Time | NT-1 | NT-2 | NT-3 | NT-4 | NT-5 |
| [NT-proBNP], pg/mL | | 5.63 | 62.01 | 327.45 | 1594.19 | 5212.03 |
| A | 0:05:00 | 0.136 | 0.501 | 2.552 | 8.993 | 44.76 |
| B | 0:03:20 | 0.111 | 0.259 | 1.272 | 5.486 | 22.575 |

Figure 10A:
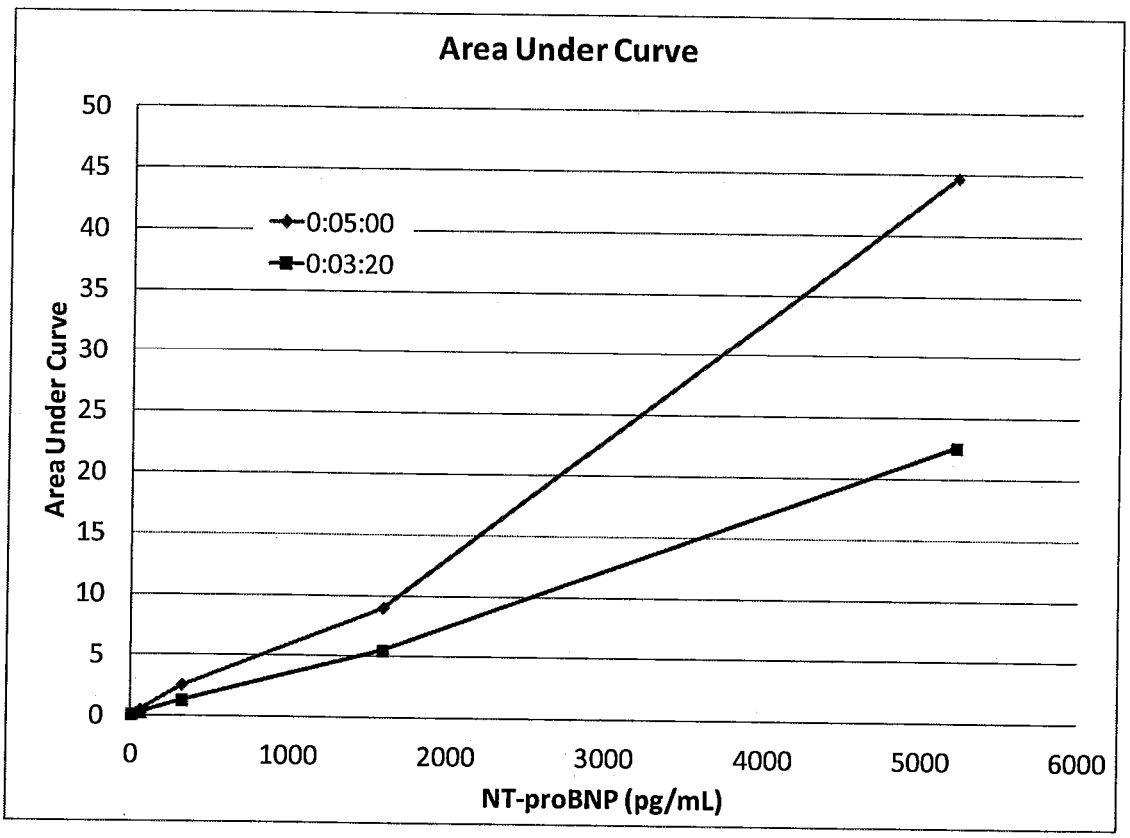
FIGS. 10A and 10B are graphs which show the difference between different fluids having no correction for reaction time and having correction for reaction time.
Figure 10B:
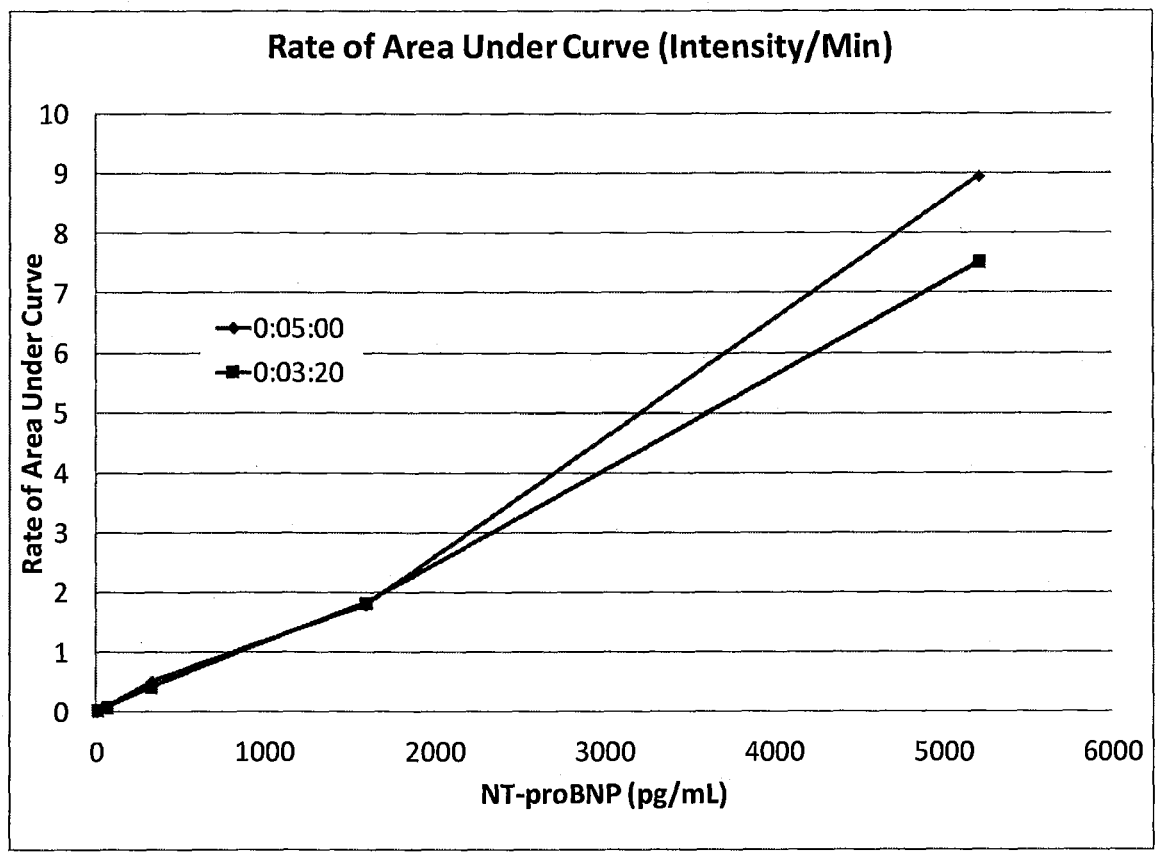

FIG. 10A shows a plot of signal intensity versus concentration of NT-proBNP. As FIG. 10A shows for equal concentrations of analyte, the detected signal is significantly greater for the assays having the longer reaction time (5 mins. vs. 3 mins and 20 secs). Using conventional calibration models would result in significantly different report results for assays having the same concentration of NT-proBNP. FIG. 10B is a plot of rate of signal versus concentration of NT-proBNP. In this graph, the reaction time is accounted for by using rate of signal as opposed to signal, per se. As a result, the rate of signal for the different reaction times are roughly the same. Therefore, the reported result of analyte concentration between the two different samples having differing reaction times will be approximately the same.

Example 2

Assay devices were prepared in a similar manner as Example 1, all using the same chip design. Two sets of samples having differing viscosities but the same concentration of NT-proBNP were prepared. The samples in Table 2 had 43.3 pg/mL of analyte. The samples in Table 3 had 750 pg/mL of NT-proBNP.

TABLE 2

| Viscosity | Concentration (pg/mL) | Total Time | Wick Time | CD Time (Min) | Signal | Predicted Conc from Signal | Rate of Signal | Predicted Conc from Rate of Signal |
|---|---|---|---|---|---|---|---|---|
| 1.42 | 43.3 | 6.73 | 5.25 | 3.55 | 0.28 | 24.61 | 0.080 | 43.29 |
| 2.43 | 43.3 | 13.00 | 10.42 | 4.93 | 0.40 | 38.44 | 0.080 | 43.52 |
| 3.71 | 43.3 | 27.13 | 22.30 | 8.02 | 0.63 | 67.65 | 0.079 | 42.66 |
| | | | | mean | 0.44 | 43.56 | 0.080 | 43.15 |
| | | | | SD | 0.18 | 21.97 | 0.001 | 0.44 |
| | | | | cv % | 40.8% | 50.4% | 0.8% | 0% |

TABLE 3

| Viscosity | Concentration (pg/mL) | Total Time | Wick Time | CD Time (Min) | Signal | Predicted Conc from Signal | Rate of Signal | Predicted Conc from Rate of Signal |
|---|---|---|---|---|---|---|---|---|
| 1.54 | 750 | 6.65 | 5.23 | 3.72 | 4.32 | 522.88 | 1.16 | 764.85 |
| 2.32 | 750 | 12.43 | 9.87 | 5.22 | 6.32 | 769.48 | 1.21 | 797.35 |

TABLE 3-continued

| Viscosity | Concentration (pg/mL) | Total Time | Wick Time | CD Time (Min) | Signal | Predicted Conc from Signal | Rate of Signal | Predicted Conc from Rate of Signal |
|---|---|---|---|---|---|---|---|---|
| 3.66 | 750 | 26.43 | 21.82 | 7.70 | 7.95 | 971.47 | 1.03 | 678.67 |
|  |  |  |  | mean | 6.20 | 754.61 | 1.14 | 746.96 |
|  |  |  |  | SD | 1.82 | 224.66 | 0.09 | 61.33 |
|  |  |  |  | cv % | 29.4% | 29.8% | 8.1% | 8.2% |

As Tables 2 and 3 show, differing viscosity samples yield differing reaction times (CD time) and differing signal strength for the same concentration of analyte. As a result, the predicted concentration for samples containing 43.3 pg/mL of analyte (Table 2) using signal alone and a calibration model that uses signal alone ranges from 24.61 to 67.65 which results in a coefficient of variation of 50.4%. For samples containing 750 mg/mL of NT-proBNP using signal alone and a calibration model that uses signal alone ranges from 522 to 971 mg/L, which results in a coefficient of variation of 29.8%. On the other hand, using rate of signal and a calibration model that uses rate of signal (signal/reaction time) yields concentrations range from 42.66 to 43.52 mg/mL (Table 2) for a cv % of 1.0%, or from 679 to 797 mg/mL (Table 3) for a cv % of 8.2%.

Figure 11A:
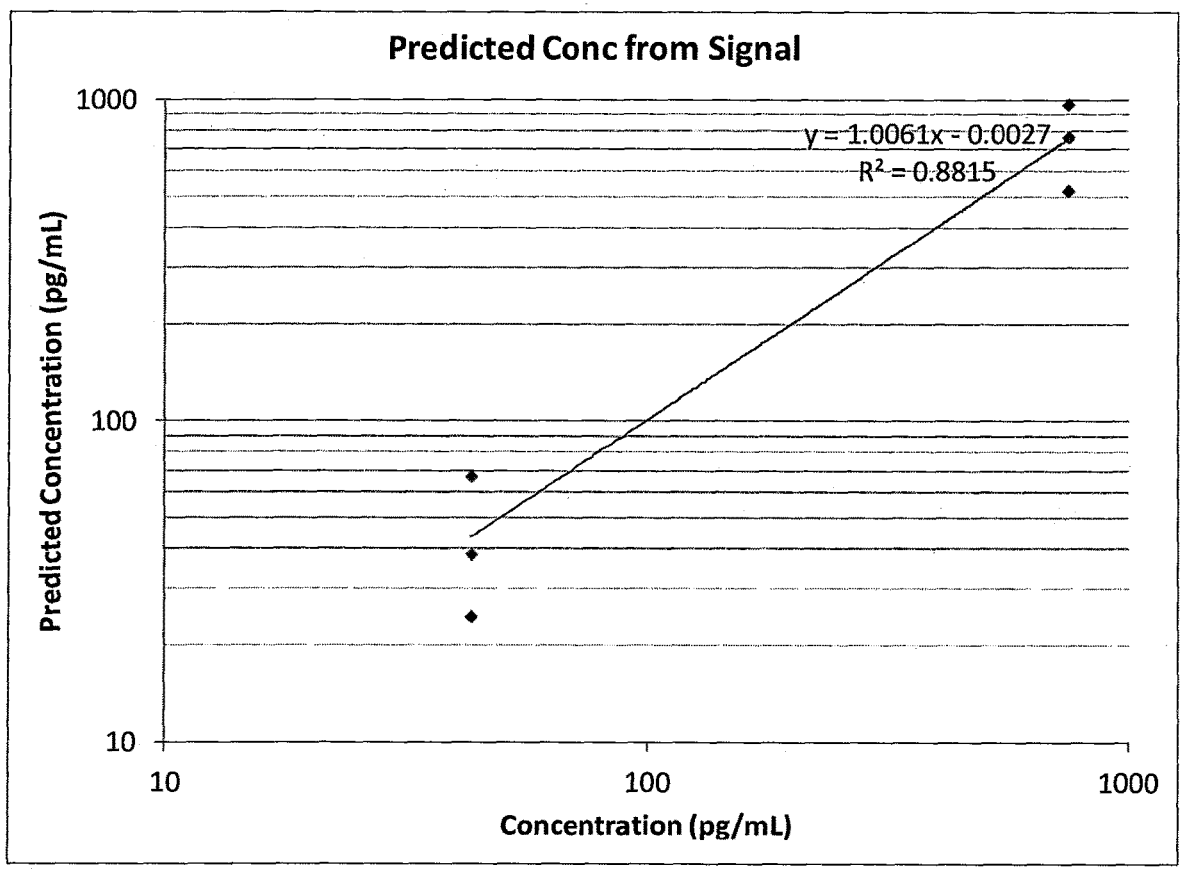
FIGS. 11A and 11B shows predicted concentration vs. actual concentration for calibration models that account for reaction time and do not account for reaction time.
Figure 11B:
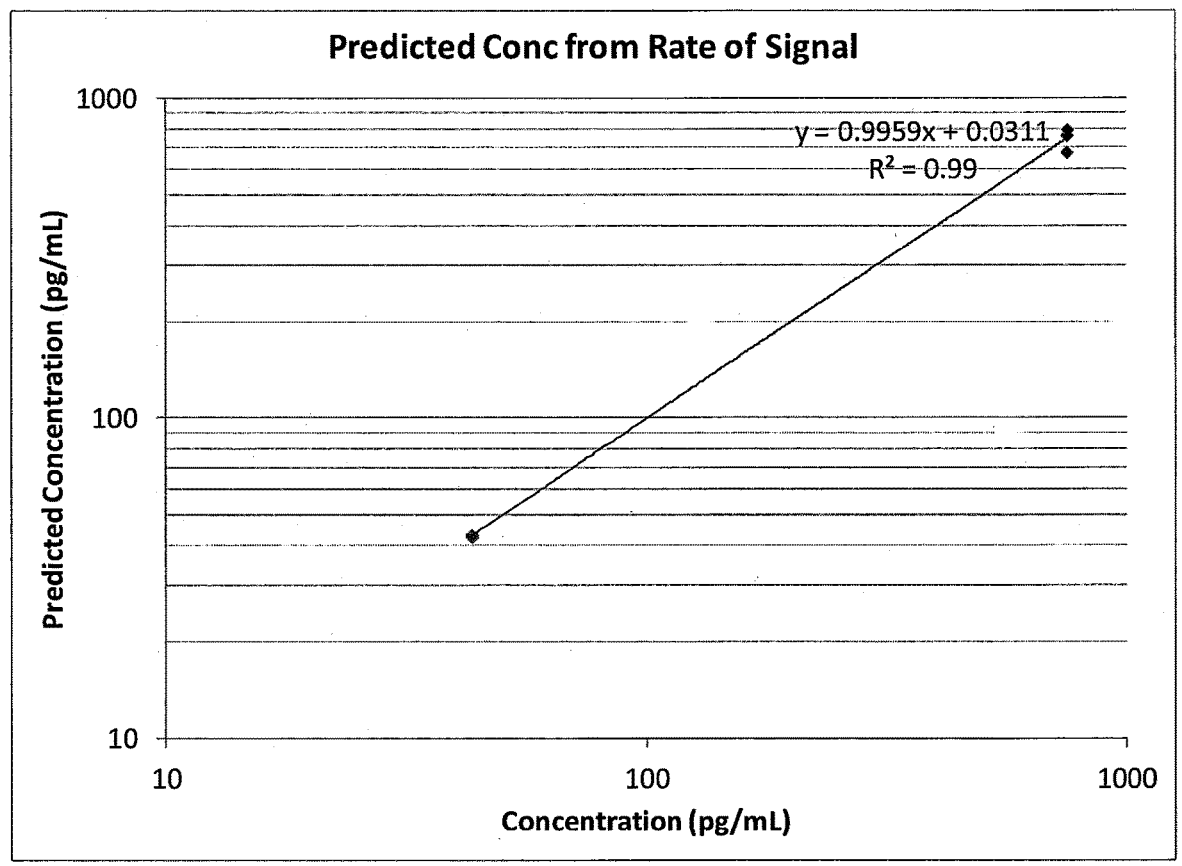

FIGS. 11A and 11B graphically represent the data from Table 3. As the Figures show the predicted concentration from using signal alone with a calibration model using signal alone (FIG. 11A) has a poor correlation with the actual concentration ($R^2$=0.8815), wherein the predicted concentration that uses signal and reaction time (i.e., rate of signal) and a calibration model that uses rate of signal (FIG. 11B) has an excellent correlation with the actual concentration ($R^2$=0.99)

Example 3

Plastic substrate chips made of Zeonor (Zeon, Japan) having oxidized dextran on the surface for covalently immobilization of proteins via Schiff base coupling were used. Two detection zones were provided to multiplex NT-proBNP and Risperidone were provided Fluorescently labeled Anti-NT-proBNP monoclonal antibody was deposited and dried to create a reagent zone. Anti-NT-proBNP monoclonal antibody was deposited and dried to create a detection zone. Fluorescently labeled BSA with covalently attached risperidone was deposited and dried to create a reagent zone. Anti-risperidone monoclonal antibody was deposited and dried to create a second detection zone. A small amount of Triton X-45 was deposited on the device to increase wettability of the sample for better capillary flow. Sample having the concentration of sample set out in Table 4 below was added to the sample zone of the device and the capillary action of the micropillar array distributed the sample through the flow channel into the wicking zone. To provide different reaction times, PVP was used to modify the viscosity to provide different viscosity serum. The signal intensities from the fluorescently labeled complexes in the detection zone were recorded in a prototype line-illuminating fluorescence scanner. The results are shown in Table 5 described below. For Tables 4 and 5, "mean CJ Diss time" is the reagent dissolution time, "approx. CJ diss volume" is the reaction volume, and "mean area" is an indication of signal strength.

TABLE 4

Higher viscosity with added PVP leads to slower flow (longer flow time) and longer conjugate dissolution time (i.e., reagent dissolution time) and less conjugate dissolution volume (i.e., reaction volume).

| Fluid | % PVP | Measured Viscosity (cP) | NTproBNP pg/mL | Risperidone ng/mL | Mean CJ Diss time | Mean total Flow time | approx CJ diss volume (uL) |
|---|---|---|---|---|---|---|---|
| Lv 1-1 | 0 | 1.42 | 30 | 28 | 0:03:37 | 0:06:44 | 4.83 |
| Lv 1-2 | 0.5 | 2.43 | 30 | 28 | 0:04:51 | 0:13:00 | 3.36 |
| Lv 1-3 | 1 | 3.71 | 30 | 28 | 0:08:11 | 0:27:08 | 2.71 |
| Lv 2-1 | 0 | 1.54 | 945 | 2.8 | 0:03:43 | 0:06:39 | 5.03 |
| Lv 2-2 | 0.5 | 2.32 | 945 | 2.8 | 0:05:13 | 0:12:26 | 3.78 |
| Lv 2-3 | 1 | 3.66 | 945 | 2.8 | 0:07:42 | 0:26:26 | 2.62 |

Table 5 shows increasing response for both NTpro-NBP and Risperidone as flow time increases.

TABLE 5

Longer flow time leads to higher signal (i.e., response) for both sandwich assay and competitive assay.

| | Measured | Flow Time | | | NTpro-BNP | | | Risperidone | | |
|---|---|---|---|---|---|---|---|---|---|---|
| Sample Fluid | Viscosity (cP) | Flow to EWZ | SD | % CV | Mean Area | SD | % CV | Mean Area | SD | % CV |
| Lv 1-1 | 1.42 | 0:06:44 | 0.0001 | 1.7892 | 0.25 | 0.09 | 38.61 | 15.79 | 2.86 | 18.10 |
| Lv 1-2 | 2.43 | 0:13:00 | 0.0002 | 2.1321 | 0.43 | 0.12 | 27.03 | 22.77 | 3.74 | 16.40 |

TABLE 5-continued

Longer flow time leads to higher signal (i.e., response) for both sandwich assay and competitive assay.

| Sample Fluid | Measured Viscosity (cP) | Flow Time Flow to EWZ | SD | % CV | NTpro-BNP Mean Area | SD | % CV | Risperidone Mean Area | SD | % CV |
|---|---|---|---|---|---|---|---|---|---|---|
| Lv 1-3 | 3.71 | 0:27:08 | 0.0010 | 5.3858 | 0.79 | 0.18 | 22.70 | 67.01 | 8.98 | 13.41 |
| Lv 2-1 | 1.54 | 0:06:39 | 0.0000 | 0.9497 | 4.32 | 0.31 | 7.06 | 15.34 | 1.51 | 9.87 |
| Lv 2-2 | 2.32 | 0:12:26 | 0.0006 | 7.5103 | 6.32 | 0.43 | 6.75 | 24.64 | 1.47 | 5.97 |
| Lv 2-3 | 3.66 | 0:26:26 | 0.0003 | 1.7393 | 7.95 | 1.51 | 18.97 | 63.70 | 12.83 | 20.15 |

As Tables 4 and 5 show, differing viscosity samples yield differing reaction times (CD time) and differing signal strength for the same concentration of analyte.

Table 6 compares the precision (% CV) of original response from samples with different viscosities vs. the two types of adjusted responses from the data from Example 3. NTproBNP is a sandwich assay and Risperidone is competitive assay.

TABLE 6

Precision for the adjusted responses for both RISP and NTproBNP are improved with either volume or time adjustment as compared to the original unadjusted response (peak area).

| Sample Fluid | Measured Viscosity (cP) | NTproBNP Mean Area | RISPMean Area | NTproBNP pg/mL | Risperidone ng/mL | Mean CJ Diss time | CJ Diss wlume (uL) | NTpro-BNP X Vol | NTpro-BNP/ Time | Risp X Vol | Risp/ Time |
|---|---|---|---|---|---|---|---|---|---|---|---|
| Lv 1-1 | 1.42 | 0.25 | 15.79 | 30 | 28 | 0:03:37 | 6.15 | 1.51 | 0.07 | 97.18 | 4.37 |
| Lv 1-2 | 2.43 | 0.43 | 22.77 | 30 | 28 | 0:04:51 | 4.19 | 1.79 | 0.09 | 95.47 | 4.70 |
| Lv 1-3 | 3.71 | 0.79 | 67.01 | 30 | 28 | 0:08:11 | 3.30 | 2.59 | 0.10 | 220.99 | 8.19 |
| Average | | 0.49 | 35.19 | | | | | 1.97 | 0.08 | 137.88 | 5.75 |
| SD | | 0.27 | 27.77 | | | | | 0.56 | 0.01 | 71.98 | 2.12 |
| CV | | 57% | 79% | | | | | 29% | 17% | 52% | 37% |
| Lv 2-1 | 1.54 | 4.32 | 15.34 | 945 | 2.8 | 0:03:43 | 6.40 | 27.64 | 1.16 | 98.17 | 4.13 |
| Lv 2-2 | 2.32 | 6.32 | 24.64 | 945 | 2.8 | 0:05:13 | 4.76 | 30.06 | 1.21 | 117.23 | 4.72 |
| Lv 2-3 | 3.66 | 7.95 | 63.70 | 945 | 2.8 | 0:07:42 | 3.19 | 25.41 | 1.03 | 203.50 | 8.27 |
| Average | | 6.20 | 34.56 | | | | | 27.70 | 1.14 | 139.63 | 5.71 |
| SD | | 1.82 | 25.66 | | | | | 2.33 | 0.09 | 56.12 | 2.24 |
| CV | | 29% | 74% | | | | | 8% | 8% | 40% | 39% |

For sample fluids Lv1, the uncorrected CV is 57%, whereas the Type 1 correction is 29% and Type 2 is 17%, a significant improvement. For risperidone, the uncorrected CV is 79%, whereas the Type 1 is 52% and Type 2 is 37%, again a significant improvement. For sample fluids Lv2, the uncorrected CV is 29%, whereas the Type 1 correction is 8% and Type 2 is 8%, a significant improvement. For risperidone, the uncorrected CV is 74%, whereas the Type 1 is 40% and Type 2 is 39%, again a significant improvement.

In another set of experiments, procalcitonin (PCT), a sandwich-type assay, was tested.

Example 4

Plastic substrate chips made of Zeonor (Zeon, Japan) having oxidized dextran on the surface for covalently immobilization of proteins via Schiff base coupling were used. Fluorescently labeled Anti-PCT monoclonal antibody was deposited and dried to create a reagent zone. Anti-PCT monoclonal antibody was deposited and dried to create a detection zone. A small amount of Triton X-45 was deposited on the device to increase wettability of the sample for better capillary flow. Sample having the concentration of PCT set out in Table 7 was added to the sample zone of the device and the capillary action of the micropillar array distributed the sample through the flow channel into the wicking zone. The viscosity was modified by adding triglycerides (Trig) in the concentration set out in Table 7 was also added to the samples (referred to as "Interferent" in Table 7). Increasing the concentration of the triglycerides increased the sample viscosity. The signal intensities (peak area) from the fluorescently labeled complexes in the detection zone were recorded in a prototype line-illuminating fluorescence scanner.

TABLE 7

Increasing triglyceride concentration in sample leads to slower flow, longer flow time and higher PCT signal.

| Fluid | # of Reps | Interferent | PCT Concentration (ng/mL) | Interferent Concenetration | Mean Flow Time to End of WZ | Peak Area Mean | SD | % CV |
|---|---|---|---|---|---|---|---|---|
| PP1 | 3 | Trig | 0.26 | 3000 | 0:15:32 | 4.68 | 0.23 | 4.86 |
| PP1 | 3 | Trig | 0.26 | 1000 | 0:08:36 | 4.33 | 0.11 | 2.52 |
| PP1 | 3 | Trig | 0.26 | 500 | 0:07:22 | 4.63 | 0.18 | 3.93 |
| PP1 | 3 | Trig | 0.26 | 250 | 0:07:09 | 3.94 | 0.23 | 5.88 |
| PP3 | 3 | Trig | 2.64 | 3000 | 0:13:55 | 47.72 | 1.17 | 2.44 |
| PP3 | 3 | Trig | 2.64 | 1000 | 0:08:32 | 42.31 | 2.85 | 6.74 |
| PP3 | 3 | Trig | 2.64 | 500 | 0:07:51 | 37.50 | 2.39 | 6.38 |
| PP3 | 3 | Trig | 2.64 | 250 | 0:07:03 | 35.03 | 2.62 | 7.48 |
| PP4 | 3 | Trig | 23.20 | 3000 | 0:14:45 | 412.76 | 21.82 | 5.29 |
| PP4 | 3 | Trig | 23.20 | 1000 | 0:08:38 | 324.85 | 23.54 | 7.25 |
| PP4 | 3 | Trig | 23.20 | 500 | 0:07:35 | 314.75 | 18.55 | 5.89 |
| PP4 | 3 | Trig | 23.20 | 250 | 0:07:03 | 291.40 | 9.37 | 3.22 |

As Table 7 shows, increased viscosity (i.e., increased concentration of Trig) leads to a longer flow time (i.e., a measure of reaction time) and hence a higher signal. This is consistent with data for other assays (both sandwich and competitive) that demonstrate increased signal with increased reaction time. In another set of experiments, total protein (from albumin and gamma-globulins) was added as a viscosity modifier. Table 8 below shows that increasing total protein concentration leads to decreasing signal (peak area) although the flow time becomes longer. This was inconsistent with the inventors' other findings. Further experiments to modify flow time (i.e., reaction time) either by modifying viscosity or modifying the assay device to affect total flow time confirmed the inventors' original findings that increased reaction time leads to increased signal. It is believed that the protein somehow interferes with the PCT and subsequently gave erroneous results.

TABLE 8

Increasing total protein concentration in sample increases the inferences on PCT, leading to a decreasing signal (the peak area) although the flow time increases with increased total protein concentration in sample.

| Fluid | # of Reps | Interferent | PCT Concentration (ng/mL) | Interferent Concenetration | Mean Flow Time to End of WZ | Peak Area Mean | SD | % CV |
|---|---|---|---|---|---|---|---|---|
| PP1 | 3 | TP | 0.25 | 12 | 0:13:50 | 3.02 | 0.14 | 4.66 |
| PP1 | 3 | TP | 0.25 | 10 | 0:10:01 | 3.30 | 0.03 | 0.83 |
| PP1 | 3 | TP | 0.25 | 8 | 0:07:48 | 3.69 | 0.35 | 9.52 |
| PP1 | 3 | TP | 0.25 | 7 | 0:06:33 | 4.34 | 0.12 | 2.81 |
| PP3 | 3 | TP | 2.50 | 12 | 0:13:46 | 29.45 | 3.96 | 13.45 |
| PP3 | 3 | TP | 2.50 | 10 | 0:10:10 | 34.48 | 1.75 | 5.06 |
| PP3 | 3 | TP | 2.50 | 8 | 0:07:53 | 42.30 | 1.44 | 3.40 |
| PP3 | 3 | TP | 2.50 | 7 | 0:06:30 | 45.49 | 0.52 | 1.14 |
| PP4 | 3 | TP | 22.00 | 12 | 0:13:27 | 263.62 | 31.51 | 11.95 |
| PP4 | 3 | TP | 22.00 | 10 | 0:09:40 | 268.13 | 21.64 | 8.07 |
| PP4 | 3 | TP | 22.00 | 8 | 0:07:48 | 359.91 | 24.13 | 6.70 |
| PP4 | 3 | TP | 22.00 | 7 | 0:06:34 | 371.20 | 4.38 | 1.18 |

Additional Embodiments

1. A method for performing an assay on a liquid sample for the detection of one or more analytes of interest in an assay device having a flow path which includes a sample zone and detection zone thereon, wherein the method comprises: dispensing the sample onto the sample zone; combining the sample and a reagent, wherein the sample and reagent may be combined prior to addition of the sample to the sample zone or on the assay device, flowing the combined sample/reagent by capillary action into and through the detection zone having capture elements bound thereto, wherein a signal at least partially representative of the presence or concentration of analyte(s) is produced and detected; determining a reaction time; and determining the concentration of the analyte by using both the detected signal and the reaction time.

2. A method as disclosed in embodiment 1, further comprising determining flow rate and determining concentration by reaction time, flow rate and detected signal.

3. A method as disclosed in embodiment 2, wherein the flow rate is represented by reaction volume which is the product of reaction time and flow rate.

4. A method as disclosed in embodiment 3, wherein the concentration is determined by adjusting the detected signal by: (1) multiplying the detected signal by reaction volume (adjusted signal (R)=detected signal×reaction volume); or (2) dividing the detected signal by the reaction time (adjusted signal (R)=response/reaction time).

5. A method as disclosed in embodiment 1, wherein the concentration is determined by adjusting the detected signal by dividing the detected signal by the reaction time (adjusted signal (R)=response/reaction time).

6. A method as disclosed in embodiment 1, wherein the reaction time is the time it takes the combined sample/reagent to pass through the detection zone.

7. A method as disclosed in embodiment 6, wherein the reaction time is determined as the reagent dissolution time, which is the time the combined sample/reagent is first detected at a point along the flow path to the time when the combined sample/reagent is no longer detected at that point in the flow path.

8. A method as disclosed in embodiment 6, wherein the reaction time is determined by detecting a signal produced by a detection element.

9. A method as disclosed in embodiment 1, wherein the sample and reagent are combined prior to being dispensed onto the sample zone.

10. A method as disclosed in embodiment 1, wherein the flow path further comprises a wicking zone located downstream from the detection zone and having a capacity to receive liquid flowing from the detection zone and further flowing the sample from the detection zone into the wicking zone.

11. A method as disclosed in embodiment 10, wherein a time proportional to reaction time is obtained by measuring the total flow time, which is the time it takes the sample to flow from the sample zone to the end of the wicking zone.

12. A method as disclosed in embodiment 10, wherein a time proportional to reaction time is obtained by measuring the total wick time, which is the time between sample entering the wicking zone to reaching the end of the wicking zone.

13. A method as disclosed in embodiment 10, wherein a time proportional to the reaction time is determined as the wetting time, which is the time required for a sample to completely penetrate throughout the assay device.

14. A method as disclosed in embodiment 1, wherein a rate inversely proportional to the reaction time is determined as the flow rate.

15. A method as disclosed in embodiment 5, wherein the concentration is determined by the adjusting the detected signal by a rate of signal R which is defined as S/t, wherein S is the detected signal and t is the reaction time.

16. A method as disclosed in embodiment 15, wherein the concentration is determined by the equation:

$$C = (R-\alpha)/\beta$$

wherein C is concentration of the analyte, R is the rate of signal, $\alpha$ is a first constant, and $\beta$ is a second constant.

17. A method as disclosed in embodiment 16, wherein $\alpha$ and $\beta$ are determined during the calibration of the assay.

18. A method as disclosed in embodiment 15, wherein the concentration is determined by the equation:

$$C = e^{\left\{-\frac{1}{\beta_3}\left[\beta_2 + \ln\left(\frac{\beta_1}{R-\beta_0}-1\right)\right]\right\}}$$

wherein C is concentration of the analyte, R is the rate of signal, and $\beta_0$-$\beta_3$ are first, second, third and fourth constants, respectively.

19. A method as disclosed in embodiment 18, wherein $\beta_0$-$\beta_3$ are determined during the calibration of the assay.

20. A method as disclosed in embodiment 1, wherein the concentration is determined by using S and t, wherein S is the detected signal and t is the reaction time.

21. A method as disclosed in embodiment 20, wherein the concentration C is determined by the equation:

$$C = \frac{1}{k}\left[\frac{S}{(\beta t + \alpha)} - b\right]$$

wherein S is the detected signal, t is the reaction time, $\alpha$ is a first constant, and $\beta$ is second constant, and k is a third constant.

22. A method as disclosed in embodiment 21, wherein $\alpha$, $\beta$ and k are determined during the calibration of the assay.

23. A method as disclosed in embodiment 20, wherein the concentration C is determined by the equation:

$$C = e^{\left\{-\frac{1}{\beta_3}\left[\beta_2 + \ln\left(\frac{\beta_1}{\frac{S}{\beta t + \alpha}-\beta_0}-1\right)\right]\right\}}$$

wherein C is concentration of the analyte, R is the rate of signal, and $\beta_0$-$\beta_3$ are first, second, third and fourth constants, respectively.

24. A method as disclosed in embodiment 23, wherein $\beta_0$-$\beta_3$ are determined during the calibration of the assay.

25. A method as disclosed in embodiment 1, wherein the step of combining the sample and a reagent further comprises, providing a reagent zone between the sample zone and detection zone containing the reagent, wherein the sample flowing from the sample zone dissolves the reagent and forms a reagent plume that comprises liquid sample and dissolved reagent.

26. A method as disclosed in embodiment 25, wherein the reaction time is proportional to a reagent dissolution time, which is proportional to the time the reagent plume of first detected at a point along the substrate to the time when the reagent plume is no longer detected.

27. A method as disclosed in embodiment 1, wherein the detection zone comprises projections which extend substantially vertically from the substrate, wherein the projections have a height, cross-section and a distance between one another that defines a capillary space between the projections capable of generating capillary flow parallel to the substrate surface.

28. A method as disclosed in embodiment 1, wherein the reagent comprises a labeled antibody conjugate which is capable of binding to the analyte in the sample in the case of a sandwich-type assay, or the reagent comprises an analyte having a labeled antibody bound thereto in the case of a competitive assay.

29. A method as disclosed in embodiment 28, wherein the assay is a sandwich-type assay.

30. A method for performing an assay on a liquid sample for the detection of one or more analytes of interest in an assay device having a flow path which includes a sample zone and detection zone thereon, wherein the method comprises: dispensing the sample onto the sample zone; combining the sample and a reagent, wherein the sample and reagent may be combined prior to addition of the sample to the sample zone or on the assay device, flowing the combined sample/reagent by capillary action into and through the detection zone having capture elements bound thereto, wherein a signal at least partially representative of the presence or concentration of analyte(s) is produced and detected; determining a reaction volume; and determining the concentration of the analyte by using both the detected signal and the reaction volume.

31. A method as disclosed in embodiment 30, wherein the reaction volume is the product of reaction time and flow rate.

32. A method as disclosed in embodiment 31, wherein the reaction time is the time it takes the combined sample/reagent to pass through the detection zone.

33. A method as disclosed in embodiment 33, wherein the reaction time is determined as the reagent dissolution time, which is the time the combined sample/reagent is first detected at a point along the flow path to the time when the combined sample/reagent is no longer detected at that point in the flow path.

34. A method of calibrating an assay comprising: (a) providing multiple calibrator fluids having known concentrations of analyte therein; (b) providing an assay device having a substrate that include a sample zone and detection zone: (c) dispensing one of the calibrator fluids onto the sample zone; (d) combining the calibrator fluid and a reagent, wherein the calibrator fluid and reagent may be combined prior to addition of the calibrator fluid to the sample zone or on the assay device, (e) flowing the combined calibrator fluid/reagent by capillary action into and through the detection zone having capture elements bound thereto, wherein a signal at least partially representative of the presence or concentration of analyte(s) is produced and detected; (f) determining a reaction time; (g) repeating steps (b)-(f) for each calibrator fluid; (h) using the detected signal S, the reaction time t and the known concentrations C to determine a calibration curve.

35. A method of calibrating an assay as disclosed in embodiment 34, wherein the reaction time is the time it takes the combined sample/reagent to pass through the detection zone.

36. A method of calibrating an assay as disclosed in embodiment 34, wherein the detected signal S, the reaction time t and the known concentrations C are used to determine the function $f$ in the relationship $S=f(C,t)$.

37. A method of calibrating an assay as disclosed in embodiment 34, wherein the function $f$ is linear and the calibration curve is defined by:

$$S=(\beta t+\alpha)(kC+b)$$

wherein $\beta$, $\alpha$, k and b are constants.

38. A method of calibrating an assay as disclosed in embodiment 35, wherein the function $f$ is non-linear and the calibration curve is defined by:

$$S = (\beta t + \alpha)\left[\beta_0 + \frac{\beta_1}{1 + e^{-(\beta_2+\beta_3 \ln C)}}\right]$$

wherein $\beta_0$-$\beta_3$ are first, second, third and fourth constants, respectively.

39. A method of calibrating an assay as disclosed in embodiment 34, wherein a rate of signal change R is calculated as R=S/t and the rate of signal and concentration are used to determine the function $f$ is the relationship R=$f$(C).

40. A method of calibrating an assay as disclosed in embodiment 39, wherein the function is linear and the calibration curve is defined by:

$$R=mC+b,$$

wherein m and b are constants.

41. A method of calibrating an assay as disclosed in embodiment 39, wherein the function is non-linear and the calibration curve is defined by:

$$R = \beta_0 + \frac{\beta_1}{1 + e^{-(\beta_2+\beta_3 \ln C)}}$$

wherein $\beta_0$-$\beta_3$ are first, second, third and fourth constants, respectively.

42. A method of calibrating an assay as disclosed in embodiment 34, further comprising providing a reagent zone, wherein the sample dissolves and combines with the reagent in the reagent zone.

43. A method as disclosed in embodiment 1, further comprising providing a reagent zone, wherein the sample dissolves and combines with the reagent in the reagent zone.

44. A method of calibrating an assay comprising: (a) providing multiple calibrator fluids having known concentrations of analyte therein; (b) providing an assay device having a substrate that include a sample zone and detection zone: (c) dispensing one of the calibrator fluids onto the sample zone; (d) combining the calibrator fluid and a reagent, wherein the calibrator fluid and reagent may be combined prior to addition of the calibrator fluid to the sample zone or on the assay device, (e) flowing the combined calibrator fluid/reagent by capillary action into and through the detection zone having capture elements bound thereto, wherein a signal at least partially representative of the presence or concentration of analyte(s) is produced and detected; (f) determining a reaction volume; (g) repeating steps (b)-(f) for each calibrator fluid; (h) using the detected signal S, the reaction volume and the known concentrations C to determine a calibration curve.

45. A method of calibrating an assay as disclosed in embodiment 44, wherein the reaction volume is determined by the product of reaction time and flow rate.

46. A method of calibrating an assay as disclosed in embodiment 45, wherein the detected signal S is adjusted by multiplying the detected signal by the reaction volume.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

Copending applications entitled "Low Volume Assay Device Having Increased Sensitivity" (Application No. 61/588,758, first named inventor: Phil Hosimer), "Assay Device Having Multiplexing" (Application No. 61/588,779, first named inventor: Sue Danielson), "Assay Device Having Multiple Reagent Cells" (Ser. No. 61/588,738, first named inventor Zhong Ding), "Assay Device Having Uniform Flow Around Corners" (Application No. 61/588,745, first named inventor James Kanaley), "Controlling Fluid Flow Through An Assay Device" (Application No. 61/588,772, first named inventor James Kanaley), and "Assay Device Having Controllable Sample Size" (Application No. 61/588,899, first named inventor, Ed Scalice), all filed Jan. 20, 2012 and all incorporated by reference in their entireties.

What is claimed is:

1. A method for performing an assay on a liquid sample for the detection of one or more analytes of interest in an assay device having a flow path which includes a sample zone and detection zone thereon, wherein the method comprises:

dispensing the sample onto the sample zone;
combining the sample and a reagent, wherein the sample and reagent may be combined prior to addition of the sample to the sample zone or on the assay device;
flowing the combined sample/reagent by capillary action into and through the detection zone having capture elements bound thereto that bind the one or more analytes, wherein signals representative of the presence or concentration of the one or more analytes are produced by detection elements that are associated with the reagent or generated through a reaction with the reagent;
determining a reaction time using the signals generated by the detection elements at points in the flow path; and
determining the concentration of the one or more analytes by dividing at least one of the detected signals by the reaction time.

2. The method as claimed in claim 1, wherein the one or more analytes is one of NT-proBNP, risperidone, or procalcitonin alone or in combination with another analyte.

3. The method as claimed in claim 1, wherein the reaction time is the time it takes the combined sample/reagent to pass from a beginning to an end of the detection zone.

4. The method as claimed in claim 3, wherein the reaction time is determined as a reagent dissolution time, which is the time the combined sample/reagent is first detected at a point along the flow path to the time when the combined sample/reagent is no longer detected at that point in the flow path.

5. The method as claimed in claim 1, wherein the sample and reagent are combined prior to being dispensed onto the sample zone.

6. The method as claimed in claim 1, wherein the flow path further comprises a wicking zone located downstream from the detection zone and having a capacity to receive liquid flowing from the detection zone and further flowing the sample from the detection zone into the wicking zone.

7. A method for performing an assay on a liquid sample for the detection of one or more analytes of interest in an assay device having a flow path which includes a sample zone, a detection zone, and a wicking zone located downstream from the detection zone, wherein the method comprises:
dispensing the sample onto the sample zone;
combining the sample and a reagent, wherein the sample and reagent may be combined prior to addition of the sample to the sample zone or on the assay device;
flowing the combined sample/reagent by capillary action into and through the detection zone having capture elements bound thereto that bind the one or more analytes, wherein signals representative of the presence or concentration of the one or more analytes is are produced by detection elements that are associated with the reagent or generated through a reaction with the reagent;
determining a reaction time by using the signals generated by the detection elements at points in the flow path; and
determining the concentration of the one or more analytes by using at least the reaction time,
wherein the flow path has a capacity to receive liquid flowing from the detection zone and further flowing the sample from the detection zone into the wicking zone, and
wherein the reaction time is determined from a time proportional to the reaction time that is obtained by measuring a total flow time, which is the time it takes the sample to flow from the sample zone to the end of the wicking zone.

8. A method for performing an assay on a liquid sample for the detection of one or more analytes of interest in an assay device having a flow path which includes a sample zone, a detection zone, and a wicking zone located downstream from the detection zone, wherein the method comprises:
dispensing the sample onto the sample zone;
combining the sample and a reagent, wherein the sample and reagent may be combined prior to addition of the sample to the sample zone or on the assay device;
flowing the combined sample/reagent by capillary action into and through the detection zone having capture elements bound thereto that bind the one or more analytes, wherein signals representative of the presence or concentration of the one or more analytes are produced by detection elements that are associated with the reagent or generated through a reaction with the reagent;
determining a reaction time by using signals generated by detection elements at points in the flow path that are indicative of a flow rate; and
determining the concentration of the one or more analytes by using at least the reaction time,
wherein the flow rate is determined as a rate that is inversely proportional to the reaction time.

9. The method as claimed in claim 1, wherein the concentration is determined by the adjusting the detected signal by a rate of signal R which is defined as S/t, wherein S is the detected signal and t is the reaction time.

10. The method as claimed in claim 9, wherein the concentration is determined by the equation:

$$C=(R-\alpha)/\beta$$

wherein C is concentration of the analyte, R is the rate of signal, $\alpha$ is a first constant, and $\beta$ is a second constant.

11. The method as claimed in claim 10, wherein $\alpha$ and $\beta$ are determined during a calibration of the assay.

12. The method as claimed in claim 1, wherein the step of combining the sample and the reagent further comprises, providing a reagent zone between the sample zone and detection zone containing the reagent, wherein the sample flowing from the sample zone dissolves the reagent and forms a reagent plume that comprises liquid sample and dissolved reagent.

13. The method as claimed in claim 12, wherein the reaction time is proportional to a reagent dissolution time, which is proportional to the time the reagent plume is first detected at a point along the substrate to the time when the reagent plume is no longer detected at the point along the substrate.

14. A method for performing an assay on a liquid sample for the detection of one or more analytes of interest in an assay device having a flow path which includes a sample zone, a detection zone, and a wicking zone located downstream from the detection zone, wherein the method comprises:
dispensing the sample onto the sample zone;
combining the sample and a reagent, wherein the sample and reagent may be combined prior to addition of the sample to the sample zone or on the assay device;
flowing the combined sample/reagent by capillary action into and through the detection zone having capture elements bound thereto that bind the one or more analytes, wherein signals representative of the presence or concentration of the one or more analytes is produced by detection elements that are associated with the reagent or generated through a reaction with the reagent;

determining a reaction time by using the signals generated by the detection elements at points in the flow path that are indicative of a flow rate; and determining the concentration of the one or more analytes by using at least the reaction time, wherein the detection zone comprises projections which extend substantially vertically from the substrate, wherein the projections have a height, cross-section and a distance between one another that defines a capillary space between the projections capable of generating capillary flow parallel to the substrate surface.

15. The method as claimed in claim 1, wherein the reagent comprises a labeled antibody conjugate which is capable of binding to the one or more analytes in the sample in the case of a sandwich-type assay, or the reagent comprises a second one or more analytes having a labeled antibody bound thereto in the case of a competitive assay.

16. The method as claimed in claim 15, wherein the assay is a sandwich-type assay.

\* \* \* \* \*